United States Patent [19]

Ledig

[11] 4,118,561
[45] Oct. 3, 1978

[54] 7-(SUBSTITUTED)-7H-PYRROLO[3,2-F]QUINAZOLINE-1,3-DIAMINES

[75] Inventor: Kurt W. Ledig, Philadelphia, Pa.

[73] Assignee: American Home Products Corporation, New York, N.Y.

[21] Appl. No.: 810,659

[22] Filed: Jun. 27, 1977

Related U.S. Application Data

[63] Continuation-in-part of Ser. No. 784,987, Apr. 6, 1977, which is a continuation-in-part of Ser. No. 704,001, Jul. 9, 1976, abandoned, which is a continuation-in-part of Ser. No. 704,002, Jul. 9, 1976, abandoned.

[51] Int. Cl.² .................. C07D 239/95; C07D 487/04
[52] U.S. Cl. .................................. 542/470; 424/251; 544/250
[58] Field of Search ................. 260/256.4 Q, 256.5 R; 542/470

[56] References Cited

U.S. PATENT DOCUMENTS

| | | | |
|---|---|---|---|
| 2,945,859 | 7/1960 | Hitchings et al. | 260/256.4 Q |
| 3,505,330 | 4/1970 | Dauoll | 260/256.4 Q |

*Primary Examiner*—Paul M. Coughlan, Jr.

[57] ABSTRACT

Pyrrolo[3,2-f]quinazoline-1,3-diamine and the 7-(substituted) and 7,8-disubstituted derivatives thereof, possess anti-bacterial activity in vitro. The invention also provides compounds having other biological effects, such as synergism in vivo with sulfa drugs against bacterial infections, activity in vivo against malarial infections, and anti-cancer activity in vivo. In addition, the compounds show anti-folic acid activity in in vitro tests.

110 Claims, No Drawings

7-(SUBSTITUTED)-7H-PYRROLO[3,2-F]QUINAZOLINE-1,3-DIAMINES

This application is a continuation-in-part of copending application Ser. No. 784,987, filed Apr. 6, 1977, which in turn is a continuation-in-part of application Ser. No. 704,001, filed July 9, 1976, and Ser. No. 704,002, filed July 9, 1976, both now abandoned.

Various derivatives of 2,4-diaminoquinazoline and 2,4,6-triaminoquinazoline are described in the literature and are known to possess antifolic activity in bacterial systems. Such compounds are also known to exhibit antibacterial or antiprotozoal activity. For example, 2,4-diaminoquinazolines having an alkyl group at the 5-position and/or 6-position or having a trimethylene bridge between the 5- and 6-position possess antibacterial activity [see Hitchings et al., U.S. Pat. No. 2,945,859 or De Graw et al., J. Med. Chem., 17, 762 (1974)]. 2,4-Diamino-6-[(arylmethyl)amino]quinazolines; 2,4-diamino-6-{[(substituted aryl)methyl]amino}-quinazolines; and 2,4-diamino-6-{[(heterocyclic)methyl]amino}-quinazolines along with derivatives having a 5-alkyl substituent or N$^6$-alkyl substituent exhibit antimalarial activity. [See Davoll et al., J. Med. Chem., 15, 812 (1972); Elslager et al., J. Med. Chem., 15, 1138 (1972); see also the review article by E. Elslager entitled, "New Perspectives on the Chemotherapy of Malaria, Filariasis, and Leprosy", Progress in Drug Research, 18, 99–172 (1974), in particular pages 111–116 and 152–154].

The pyrrolo[3,2-f]quinazoline-1,3-diamines of the invention differ from the known 2,4,6-triaminoquinazolines in that the 5-position and the N$^6$ position of the latter are bridged by an ethylene moiety thus forming a novel tricyclic heterocycle.

The invention sought to be patented comprises compounds of the formula:

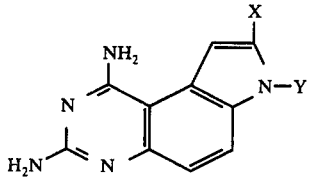

I or a non-toxic acid addition salt thereof, wherein:
(a) X is hydrogen and
Y is —CH$_2$R or —R$^1$
wherein:
R is hydrogen; methyl; ethyl; n-propyl; i-propyl; n-butyl; i-butyl; n-pentyl; n-hexyl; 2-methyl-1-propenyl; cyclobutyl; cyclopentyl; cyclohexyl; 2-phenylethyl; 2-phenylvinyl; phenyl; phenyl monosubstituted in the 2-, 3-, or 4-position by chlorine, bromine, iodine, fluorine, trifluoromethyl, methyl, ethyl, n-propyl, i-propyl, n-butyl, i-butyl, t-butyl, methoxy, ethoxy, n-propoxy, trifluoromethoxy, cyano, methylsulfonyl, acetyl, propionyl, methylthio, ethylthio, carbethoxy, carboxyl, sodium carboxy, or potassium carboxy; phenyl monosubstituted in the 3-position by amino or nitro; phenyl disubstituted in the 2,3-, 2,4-, 2,5-, 2,6-, 3,4-, or 3,5-positions by methyl, ethyl, n-propyl, methoxy, ethoxy, n-propoxy, chlorine, bromine, iodine, or fluorine; phenyl trisubstituted in the 2,4,6- or 3,4,5-positions by methyl, ethyl, methoxy, or ethoxy; 2,3,5,6-tetramethylphenyl; 3,4-(methylene dioxy)phenyl; 1-naphthalenyl; 2-naphthalenyl; 2-methyl-1-naphthalenyl; 1-bromo-2-naphthalenyl; 2-pyridinyl; 3-pyridinyl; 4-pyridinyl; 2-quinolinyl; 8-quinolinyl; 2-thienyl; 3-thienyl; 4-thiazolyl; 3,5-dimethyl-4-isoxazolyl; tetrahydro-2-furanyl; or benzo[b]thien-3-yl; and
R$^1$ is hydrogen; phenyl monosubstituted in the 2- or 4-position by amino, nitro, cyano, acetyl, propionyl, methylsulfonyl, trifluoromethyl, or carbethoxy; 2,4-dinitrophenyl; 2,4-diaminophenyl; 2-cyano-4-nitrophenyl; 2-cyano-4-aminophenyl; 3-methyl-4-nitrophenyl; 3-methyl-4-aminophenyl; 2-trifluoromethyl-4-nitrophenyl; 2-trifluoromethyl-4-aminophenyl; 2-thiazolyl; 2-pyridinyl; 5-nitro-2-pyridinyl; 2-pyrimidinyl; 2-pyrazinyl; 2-quinolinyl; 4-quinolinyl; 4-methyl-2-quinolinyl; 7-chloro-4-quinolinyl; 7-trifluoromethyl-4-quinolinyl; 2-methyl-4-quinolinyl; 3-methyl-2-quinoxalinyl; 2-phenyl-4-quinolinyl; or 2-benzothiazolyl; 5-amino-2-pyridinyl; and (b) X is methyl, phenyl, or chlorine; and
Y is hydrogen, methyl, benzyl, 3-cyanobenzyl, 4-cyanobenzyl, or 2,5-dimethylbenzyl; provided that when X is phenyl, Y may only be hydrogen or methyl, and when X is chlorine, Y may only be benzyl.

The terms "disubstituted" and "trisubstituted", as applied to substitutents on the phenyl ring of the compounds of Formula I, refer to compounds wherein the substituents are identical for example, dichlorophenyl, dimethylphenyl, dimethoxyphenyl, trimethylphenyl, trimethoxyphenyl, or the like.

In subgeneric aspects, the invention comprises the following embodiments:
(a) A compound of the general formula:

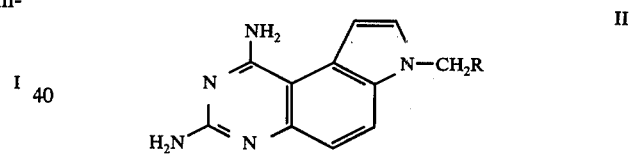

II or a non-toxic acid addition salt thereof, wherein:
R is hydrogen; methyl; ethyl; n-propyl; i-propyl; n-butyl; i-butyl, n-pentyl; n-hexyl; 2-methyl-1-propenyl; cyclobutyl; cyclopentyl; cyclohexyl; 2-phenylethyl; 2-phenylvinyl; phenyl; phenyl monosubstituted in the 2-, 3-, or 4-position by chlorine, bromine, iodine, fluorine, trifluoromethyl, methyl, ethyl, n-propyl, i-propyl, n-butyl, i-butyl, t-butyl, methoxy, ethoxy, n-propoxy, trifluoromethoxy, cyano, methylsulfonyl, acetyl, propionyl, methylthio, ethylthio, carbethoxy, carboxyl, sodium carboxy, or potassium carboxy; phenyl monosubstituted in the 3-position by amino or nitro; phenyl disubstituted in the 2,3-, 2,4-, 2,5-, 2,6-, 3,4-, or 3,5-positions by methyl, ethyl, n-propyl, methoxy, ethoxy, n-propoxy, chlorine, bromine, iodine, or fluorine; phenyl trisubstituted in the 2,4,6- or 3,4,5-positions by methyl, ethyl, methoxy, or ethoxy; 2,3,5,6-tetramethylphenyl; 3,4-(methylene dioxy)phenyl; 1-naphthalenyl; 2-naphthalenyl; 2-methyl-1-naphthalenyl; 1-bromo-2-naphthalenyl; 2-pyridinyl; 3-pyridinyl; 4-pyridinyl; 2-quinolinyl; 8-quinolinyl; 2-thienyl; 3-thienyl; 4-thiazolyl; 3,5-dimethyl-4-isoxazolyl; tetrahydro-2-furanyl; or benzo-[b]thien-3-yl;
(b) A compound of the general formula:

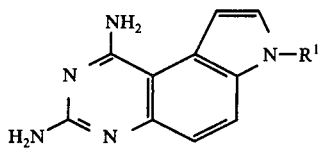

or a non-toxic acid addition salt thereof, wherein:

R[1] is hydrogen, phenyl monosubstituted in the 2- or 4-position by amino, nitro, cyano, acetyl, propionyl, methylsulfonyl, trifluoromethyl, or carbethoxy; 2,4-dinitrophenyl; 2,4-diaminophenyl; 2-cyano-4-nitrophenyl; 2-cyano-4-aminophenyl; 3-methyl-4-nitrophenyl; 3-methyl-4-aminophenyl; 2-trifluoromethyl-4-nitrophenyl; 2-trifluoromethyl-4-aminophenyl; 2-thiazolyl; 2-pyridinyl; 5-nitro-2-pyridinyl; 2-pyrimidinyl; 2-pyrazinyl; 2-quinolinyl; 4-quinolinyl; 4-methyl-2-quinolinyl; 7-chloro-4-quinolinyl; 7-trifluoromethyl-4-quinolinyl; 2-methyl-4-quinolinyl; 3-methyl-2-quinoxalinyl; 2-phenyl-4-quinolinyl; 2-benzothiazolyl; or 5-amino-2-pyridinyl;

(c) A compound of general formula:

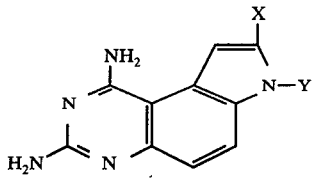

or a non-toxic acid addition salt thereof, wherein:
X is methyl, phenyl, or chlorine; and
Y is hydrogen, methyl, benzyl, 3-cyanobenzyl, 4-cyanobenzyl, or 2,5-dimethylbenzyl; provided that when X is phenyl, Y may only be hydrogen or methyl, and when X is chlorine, Y may only be benzyl.

Of special interest are the compounds 7H-pyrrolo[3,2-f]quinazoline-1,3-diamine and the derivatives thereof having an 8-methyl or 8-phenyl substituent, which compounds can be used as intermediates for preparing the compounds of Formula I having a substituent at the N[7]-position.

The compounds of Formula I, wherein Y, X, R, and R[1] are as hereinbefore defined or the salts thereof, inhibit the growth of bacteria in vitro as demonstrated in a standard tube dilution test employing seed agar or Wellcotest Sensitivity Test Agar fortified with 5% hemolyzed horse blood as the growth medium. The compounds have shown activity in vitro against one or more of the following strains of bacteria: *S. aureus smith*, *S. aureus* 53-180, *N. catarrhalis* 8193, *E. coli* 9637, *S. paratyphi* 11737, *K. pneumoniae* 10031, or *P. vulgaris* 6896. When tested in the above-described tube-dilution test, the compounds gave MIC values ranging from <0.0009 δ/ml. to 250 δ/ml. against the test organisms.

In addition the compounds of Formula I exhibit in vitro antifolic acid activity, as demonstrated by the inhibition of *Streptoccus faecalis* ATCC 8043 grown in a folic acid medium.

The invention also provides compounds which will potentiate the antibacterial effects of sulfa drugs. When tested by the oral route of administration in mice, the following compounds gave a synergistic effect with sulfamethoxazole against bacterial infections:

7-(phenylmethyl)-7H-pyrrolo[3,2-f]quinazoline-1,3-diamine;
7-[(4-fluorophenyl)methyl]-7H-pyrrolo[3,2-f]-quinazoline-1,3-diamine;
7-[(4-cyanophenyl)methyl]-7H-pyrrolo[3,2-f]-quinazoline-1,3-diamine;
7-[(3-cyanophenyl)methyl]-7H-pyrrolo[3,2-f]-quinazoline-1,3-diamine;
8-methyl-7-(phenylmethyl)-7H-pyrrolo[3,2-f]-quinazoline-1,3-diamine;
7-(4-cyanophenyl)-7H-pyrrolo[3,2-f]quinazoline-1,3-diamine; and
7-(2-thiazolyl)-7H-pyrrolo[3,2-f]quinazoline-1,3-diamine.

In addition, the invention provides compounds which have antimalarial activity in vivo as evidenced by a standard blood schizonticidal test in mice infected with Plasmodium berghei KBG 173. The compounds of Formula I possessing antimalarial activity are those wherein:

(a) X is hydrogen and
Y is —CH$_2$R
wherein:
R is i-butyl; n-hexyl; 2-methyl-1-propenyl; cyclobutyl; cyclopentyl; cyclohexyl; 2-phenylethyl; phenyl; phenyl monosubstituted in the 2-, 3-, or 4-position by chlorine, bromine, iodine, fluorine, methyl, ethyl, n-propyl i-propyl, cyano, methoxy, methylsulfonyl, acetyl, propionyl, methylthio, ethylthio, carbethoxy, trifluoromethoxy; 2-trifluoromethyl; 3-trifluoromethyl, phenyl monosubstituted in the 3-position by amino or nitro; phenyl disubstituted in the 2,3-, 2,4-, 2,5-, 2,6-, 3,4-, or 3,5-positions by methyl, ethyl, n-propyl, methoxy, chlorine, bromine, iodine, or fluorine; 2,4,6-trimethylphenyl; 3,4,5-trimethoxyphenyl; 3,4-(methylenedioxy)phenyl; 1-naphthalenyl; 2-naphthalenyl; 2-methyl-1-naphthalenyl; 2-pyridinyl; 3-pyridinyl; 4-pyridinyl; 2-quinolinyl; 8-quinolinyl; or 3-thienyl;

(b) X is hydrogen and
Y is R[1] wherein R[1] is phenyl monosubstituted in the 2- or 4-position by nitro, or acetyl; 4-cyanophenyl; 3-methyl-4-nitrophenyl; 2-thiazolyl; or 5-nitro-2-pyridinyl;

(c) X is methyl and
Y is hydrogen or 2,5-dimethylbenzyl.

Activity has also been demonstrated in vivo against P. cynomolgi infections in Rhesus monkeys as evidenced by the testing of 7-(phenylmethyl)-7H-pyrrolo[3,2-f]quinazoline-1,3-diamine; 7-[(4-methoxyphenyl)methyl]-7H-pyrrolo[3,2-f]quinazoline-1,3-diamine; and 7-[(2,5-dimethylphenyl)methyl]-7H-pyrrolo[3,2-f]quinazoline-1,3-diamine. The CD$_{50}$ doses of said compounds are 0.1 mg/kg/day, 0.316 mg/kg/day, and 1.0 mg/kg/day, respectively, after administration of the compound orally for seven days.

Activity against strains of P. berghei resistant to chloroquine, sulfones, cycloguanil, and pyrimethamine, is shown by the testing of 7-(phenylmethyl)-7H-pyrrolo[3,2-f]quinazoline-1,3-diamine and 7-[(2,5-dimethylphenyl)methyl]-7H-pyrrolo[3,2-f]quinazoline-1,3-diamine in mice against such resistant strains.

Certain compounds also possess in vivo activity in mice (I.P.) against lymphocytic leukemia P-388 when tested according to the procedure described in *Cancer Chemotherapy Reports*, Volume 3, No. 2, page 9 (Protocol 1.200), September, 1972. The compounds of Formula I wherein X is hydrogen and Y is —CH$_2$R showing such activity are:

| R | Dose (mg/kg) | T/C, % |
|---|---|---|
| phenyl | 10 | 149 |
| 4-cyanophenyl[a] | 20 | 138 |
| 4-methylsulfonyl | 10 | 136 |
| 4-carbethoxyphenyl | 10 | 141 |
| 3-nitrophenyl | 5 | 163 |
| 4-methylphenyl | 10 | 138 |
| 2,5-dimethylphenyl | 10 | 142 |
| 3,4-dimethylphenyl | 10 | 139 |
| 4-t-butylphenyl | 5 | 125 |
| 3,4-dimethoxyphenyl | 10 | 174 |
| 3,4,5-trimethoxyphenyl | 10 | 163 |
| 3-aminophenyl[b] | 10 | 165 |
| 3-thienyl | 10 | 147 |
| 2-pyridinyl | 20 | 146 |
| 4-pyridinyl | 15 | 142 |
| 2-quinolinyl | 10 | 145 |

[a]Tested as the 1/5 hydrate; and
[b]Tested as the dihydrochloride-monohydrate.

In general, the compounds of Formula I having an $N^7$-substituent are prepared by reacting 7H-pyrrolo[3,2-f]quinazoline-1,3-diamine, or the 8-methyl or 8-phenyl derivatives thereof, with an alkali metal base to form the corresponding alkali metal salt, and the salt is reacted with the appropriate reagent, $RCH_2$—Z or $R^1$—Z, in order to attach the desired substituent, $RCH_2$— or $R^1$—, at the 7-position. The base employed in the first step must be of sufficient strength to remove the proton from the indolic nitrogen of the starting material. Examples of such bases are sodium and potassium hydride, potassium t-butoxide, and lithium or potassium amide.

In the reagents $RCH_2$—Z or $R^1$—Z, R and $R^1$ are as defined hereinbefore with respect to Formula I (except that R and $R^1$ cannot be a group which contains a free amino group as a substituent) and Z is a leaving group.

When the reagent is $RCH_2$—Z, the preferred leaving group Z is a chlorine, bromine, or iodine atom. When the reagent is $R^1$—Z, the preferred leaving group is a fluorine, bromine, chlorine, or iodine atom. Other examples, of appropriate leaving groups (Z) for $RCH_2$—Z are tosyloxy or mesyloxy. The reaction is conveniently carried out in an inert solvent, such as dimethylformamide (DMF) or dimethylacetamide (DMA). In a preferred method, the 7-H-pyrrolo[3,2-f]quinazoline-1,3-diamine (VI) is treated with sodium-hydride in dimethylformamide and the appropriate reagent ($RCH_2$—Z or $R^1$—Z) is added to the reaction mixture. In the reaction employing the reagent $R^1$—Z, it is preferred to heat the reaction mixture at a temperature above 50° C.

7-H-Pyrrolo[3,2-f]quinazoline-1,3-diamine and the 8-methyl or 8-phenyl derivatives thereof, are prepared by heating an acid addition salt of a 5-aminoindole of the formula:

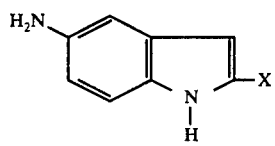

wherein X is hydrogen, methyl, or phenyl at a temperature of about 185°-215° C. with an alkali metal dicyanamide, such as sodium or potassium dicyanamide, in an aliphatic alcohol solvent. Best results are achieved if a >2:1 molar ratio of the dicyanamide to the 5-aminoindole acid addition salt is employed. A molar ratio of about 2.5:1 is preferred. The reaction is conveniently carried out by heating the reactants at the reflux temperature of the solvent. Aliphatic alcohols having a boiling point of about 185° C. to about 215° C. are preferred solvents. In a preferred method, the 5-aminoindole acid addition salt is heated at reflux temperature in 1-octyl alcohol with sodium dicyanamide until the reaction is complete.

When it is desired to prepare a compound of Formula I, wherein Y is —$CH_2R$, such compounds can be prepared by heating a compound of the formula:

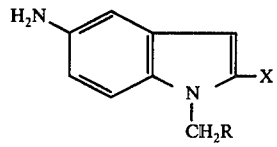

wherein X is hydrogen, methyl, phenyl, or chlorine, and R is as hereinbefore defined with respect to Formula I (provided that R cannot be a group which contains a free amino group as a substituent), with sodium or potassium dicyanamide, under the same reaction conditions as discussed previously. This process yields the 7-substituted product in one step without the need for the additional alkylation step. For example, 7-phenylmethyl-7-H-pyrrolo[3,2-f]quinazoline-1,3-diamine can be prepared by heating 5-amino-1-(phenylmethyl)indole with sodium dicyanamide in 1-octanol at the reflux temperature.

When it is desired to prepare a compound of Formula I wherein —$CH_2$—R or $R^1$ contain a free aromatic amino group, such compound can be conveniently prepared by reduction of a corresponding aromatic nitro compound. For example, 7-[(3-aminophenyl)methyl]-7H-pyrrolo[3,2-f]quinazoline-1,3-diamine is prepared by hydrogenating 7-[(3-nitrophenyl)methyl]-7H-pyrrolo[3,2-f]quinazoline-1,3-diamine in the presence of 10% palladium-carbon.

The starting materials which are the 5-aminoindoles and the reagents $RCH_2$—Z and $R^1$—Z are either known compounds or can be prepared by known methods for analogous compounds or by obvious modifications of the known methods.

The compounds of Formula I may be isolated and purified either in the form of the free bases or the acid addition salts. Methods for converting one such form to another will be obvious to one skilled in the art of chemistry.

For pharmacological use, the compounds of Formula I may be administered in the form of an acid addition salt of a non-toxic organic or inorganic acid. The salts may be prepared by methods well known in the art. Appropriate salts are those formed from the following acids: hydrochloric, hydrobromic, maleic, benzoic, pamoic, methanesulfonic, or acetic.

For pharmacological use, the compounds of Formula I may be administered alone or in combination with pharmaceutically acceptable carriers, the proportion and nature of which are determined by the solubility and chemical properties of the compound selected, the chosen route of administration, and standard pharmaceutical practice. For example, the compounds of Formula I may be administered orally in solid dosage forms, e.g. capsules, tablets, or powders, or in liquid forms, e.g. solutions or suspensions. The compounds may also be injected parenterally in the form of sterile solutions or suspensions. Solid oral forms may contain conventional excipients, for instance: lactose, succrose, magnesium stearate, resins, and like materials. Liquid oral forms may contain various flavoring, coloring, preserving, stabilizing, solublizing or suspending agents. Parenteral preparations are sterile aqueous or non-aqueous solutions or suspensions which may contain various preserving, stabilizing, buffering, solubilizing, or suspending agents. If desired, additives, such as saline or glucose may be added to make the solutions isotonic.

The following examples are illustrative of the methods of making and using the compounds of the invention. All temperatures are in centigrade.

EXAMPLE 1

7-H-Pyrrolo[3,2-f]quinazoline-1,3-diamine

A suspension of 168.5 g. 5-aminoindole hydrochloride (prepared by treating a methanolic suspension of 5-aminoindole with excess isopropanolic hydrogen chloride and diluting the salt solution with ether), 222 g. sodium dicyanamide (previously recrystallized from methanol), and 3 l. 1-octanol are refluxed with thorough stirring (under nitrogen) for 13 hours, and the hot mixture is filtered. The insolubles are washed with 500 ml. hot 1-octanol; the combined filtrates are diluted with an equal volume of ether and are acidified to pH 1 with isopropanolic hydrogen chloride. A fine, yellow precipitate is collected by filtration (slow) and is dissolved in 3 l. warm water. The aqueous solution is filtered through a coarse, sintered glass funnel. Upon cooling to ca. 25° C., the solution is washed with ethyl acetate and with ether. Basification of the solution with aqueous sodium hydroxide affords a yellow precipitate which is collected, thoroughly washed with water and dried to constant weight. The crude product (141.5 g.) is dissolved in ca. 10 l. methanol, treated with charcoal, and filtered thru Celite. The methanolic solution is concentrated to a volume of ca. 400 ml., diluted with 200 ml. acetone and chilled.

The solid that separates is washed with cold acetone and is dried to provide 77.6 g. of the title compound, m.p. 263°–265° (dec.). An additional 17.2 g. of product [m.p. 262°–264° (dec.)] are isolated by concentrating the crystallization mother liquor to a volume of ca. 40 ml., adding 40 ml. acetone, and chilling. Recrystallization of a 1.0 g. quantity of product [m.p. 263°–265° (dec.)] methanol-acetone gives 395 mg. title compound, m.p. 264° (dec.); NMR (dDMSO); $\delta$ 7.14 (doublet, J-3Hz, 9H), 7.20 (doublet, J-9Hz, 5 or 6H), 7.54 (doublet, J-3Hz, 8H), 7.78 (doublet, J-9Hz, 5 or 6H), 11.65 (broad singlet, exchangeable, 7H) p.p.m.; $\lambda_{max}^{95\% \, EtOH}$ 232.5 ($\epsilon$ 24,300), 258 ($\epsilon$ 22,120), 312 ($\epsilon$ 8,090), 340.5 ($\epsilon$ 7,420) nm; $\lambda_{min}^{95\% \, EtOH}$ 250 ($\epsilon$ 20,940), 279 ($\epsilon$ 2,310), 330 ($\epsilon$ 7,140) nm.

7-H-Pyrrolo[3,2-f]quinazoline-1,3-diamine (5.62 g. prepared in a manner similar to that described above) in 300 ml. methanol is treated with excess isopropanolic hydrogen chloride, and the solution is concentrated to a volume of ca. 100 ml., diluted with 200 ml. dimethoxyethane, and thoroughly cooled. The salt is collected and dried. Weight 2.7 g. Concentration of the mother liquor provides an additional 3.8 g. salt. Recrystallization of the two solids from methanolethanol yields 5.26 g. title compound as the monohydrochloride salt m.p. >310°.

Analysis for: $C_{10}H_9N_5 \cdot HCl$: Calculated: C, 50.96; H, 4.28; N, 29.72; Cl, 15.05. Found: C, 50.81; H, 4.22; N, 30.01; Cl, 14.88.

Employing conditions similar to those above, A. Rosowsky and N. Papathanasopoulos [J. Org. Chem., 39, 3293 (1974)] converted naphthylamines into 2,4-diaminobenzo[h]-quinazolines.

EXAMPLE 2

Method A

7-(Phenylmethyl)-7H-pyrrolo[3,2-f]quinazoline-1,3-diamine

A suspension of 13.95 g. 7H-pyrrolo[3,2-f]quinazoline-1,3-diamine in 600 ml. dry dimethylformamide is stirred under nitrogen as 3.70 g. ca. 50% sodium hydride-mineral oil dispersion is added carefully. After stirring for 1.5 hours, a solution of 9.30 g. benzyl chloride (8.5 ml.) in 20 ml. dry dimethylformamide is added during ca. 10 min. Stirring is continued for 5 hours and then 120 ml. gl. acetic acid is added to the reaction mixture. After removal of solvent (in vacuo), the residue is stirred thoroughly with excess aqueous potassium carbonate solution and filtered. The solids are collected, washed with water, and dried. The crude product is dissolved in 1.4 l. boiling methanol, treated with charcoal, and filtered through Celite. The filtrate is concentrated to ca. 125 ml. and chilled. The crystalline solid is collected, washed with acetone, and again recrystallized from methanol to afford 11.76 g. title compound, m.p. 228°, NMR (dDMSO): $\delta$ 5.53 (singlet, N-$CH_2C_6H_5$), 7.12 (doublet, J-3Hz, 9H), 7.23 (doublet, 8Hz, 5 or 6H), 7.63 (doublet, J=3Hz, 8H), 7.77 (doublet, J=9Hz, 5 or 6H) p.p.m.; $\lambda_{max}^{95\% \, EtOH}$ 235 ($\epsilon$ 26,900), 260 ($\epsilon$ 28,620), 317 ($\epsilon$ 9,640), 345 sh ($\epsilon$ 7,520) nm; $\lambda_{min}^{95\% \, EtOH}$ 243 ($\epsilon$ 26,020), 281 ($\epsilon$ 2,430) nm.

A solution of 4.5 g. 7-(phenylmethyl)-7H-pyrrolo-[3,2-f]quinazoline-1,3-diamine (prepared in a manner similar to that described above) in 300 ml. methanol-3-ml. gl. acetic acid is concentrated to ca. 100 ml. total volume, cooled, diluted with 100 ml. acetone and filtered to give 2.5 g. salt. Concentration of the mother liquor to a volume of ca. 40 ml., dilution with 40 ml. acetone and filtration provide 2.0 g. salt. The two lots of salt are combined and recrystallized from methanol-acetone to give 2.88 g. title compound as the monoacetate salt, m.p. 226° (dec).

Method B

7-(Phenylmethyl)-7H-pyrrolo[3,2-f]quinazoline-1,3-diamine

A suspension of 16.215 g. of 5-nitroindole in 1.25 l. dry dimethylformamide is stirred under nitrogen as 5.280 g. of ca. 50% sodium hydride-mineral oil dispersion is added. After stirring for 1.5 hours, a solution of 13.3 g. benzylchloride (12.1 ml.) in 25 ml. dry dimethylformamide is added and stirring is continued for 5 hours. After the addition of 175 ml. of acetic acid, the solvent is removed (in vacuo) and the residue is stirred with an excess of aqueous potassium carbonate solution and filtered. The solids are collected, washed with water and dried. The crude product is dissolved in 2.5 l. boiling methanol, treated with charcoal, and filtered through Celite. The filtrate is concentrated to ca. 400 ml. and chilled. The crystalline solid is collected to afford 20.3 g. of solid, m.p. 104°–105°. A 4.0 g. sample is recrystallized from methanol to give 3.6 g. of 1-benzyl-5-nitroindole, m.p. 103°.

Analysis for: $C_{15}H_{12}N_2O_2$: Calculated: C, 71.41; H, 4.80; N, 11.11. Found: C, 71.31; H, 4.84; N, 11.02.

A suspension of 15.3 g. of 1-benzyl-5-nitroindole, 1.0 g. palladium on carbon (10%), in 400 ml. ethyl alcohol is hydrogenated at 1 atmosphere until the hydrogen uptake ceased. The suspension is filtered and the solvent removed. The resulting solid is dissolved in 50 ml. methyl alcohol made acidic with isopropanolic hydrogen chloride and the 5-amino-1-benzylindole, hydrochloride is precipitated by the addition of 450 ml. of ether; m.p. 244°–245° dec.

Analysis for: $C_{15}H_{14}N_2 \cdot HCl$: Calculated: C, 69.89; H, 5.87; N, 10.87; Cl, 13.37. Found: C, 69.54; H, 5.73; N, 10.91; Cl, 13.63.

A suspension of 2.578 g. of 5-amino-1-benzylindole, hydrochloride, 2.228 g. sodium dicyanamide (previously recrystallized from methanol), and ca. 50 ml. dry octanol is refluxed with thorough stirring (under nitrogen) for 4 hours. The reaction mixture is filtered and the filtrate is diluted with 150 ml. ether. The precipitate which is obtained upon acidification with isopropanolic hydrogen chloride is filtered and is recrystallized from methanol to afford 0.3 g. of a salt. A solution of 3 ml. 1 N sodium hydroxide and 1 ml. methyl alcohol is thoroughly mixed with the above salt and the resulting compound is recrystallized from methanol to afford the title compound, m.p. 223°–224°, which is identical with the compound produced in Example 2, method A, based on mixture melting point and NMR spectral comparisons.

EXAMPLES 3–60

Employing conditions similar to those recorded in Example 2, 7H-pyrrolo[3,2-f]quinazoline-1,3-diamine, in dimethylformamide, is converted to the Nind-sodium salt with ca. 50% sodium hydride-mineral oil dispersion and the salt is reacted with the indicated halide for the specified period to provide the 7-(substituted)methyl-7-H-pyrrolo[3,2-f]quinazoline-1,3-diamines described on Table I.

TABLE I 7-(Substituted)-7-H-pyrrolo[3,2-f]quinazoline-1,3-diamines

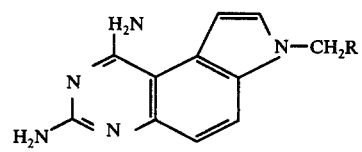

| Example No. | R | Alkylating Agent | Reax. Time (hours) | Recryst. Solv.[a] | m.p., ° C |
|---|---|---|---|---|---|
| 3 | 2-fluorophenyl | 2-fluorobenzyl chloride | 5 | M | 215–216 |
| 4 | 3-fluorophenyl | 3-fluorobenzyl chloride | 5 | M | 245–247 |
| 5 | 4-fluorophenyl | 4-fluorobenzyl chloride | 6 | M-P-B, P | 203 |
| 6 | 2-chlorophenyl | 2-chlorobenzyl chloride | 2 | M | 229 |
| 7 | 3-chlorophenyl | 3-chlorobenzyl chloride | 5 | M | 253–254 |
| 8 | 4-chlorophenyl | 4-chlorobenzyl chloride | 3 | M | 217–218 |
| 9 | 2,6-dichlorophenyl | α,2,6-trichlorotoluene | 5 | D | 307–308 (softens 298) |
| 10 | 3,4-dichlorophenyl | α,3,4-trichlorotoluene | 4 | N-W, M-P | 253–255 (dec) |
| 11 | 2-trifluoromethylphenyl | (2-trifluoromethyl)benzyl bromide | 5 | M | >310[b] (softens 230) |
| 12 | 3-trifluoromethylphenyl | (3-trifluoromethyl)benzyl chloride | 5 | M, B | 204–205 |
| 13 | 4-trifluoromethylphenyl | (4-trifluoromethyl)benzyl bromide | 1 | M | [c] |
| 14 | 2-cyanophenyl | 2-cyanobenzyl bromide | 5 | A, M | 176–180 |
| 15 | 3-cyanophenyl | 3-cyanobenzyl bromide | 5 | M[d] | 239–240 |
| 16 | 4-cyanophenyl | 4-cyanobenzyl bromide | 1 | M | 247–249 (softens 160) |
| 17 | 4-carbethoxyphenyl | 4-carbethoxybenzyl bromide[e] | 5 | E | 212–215 |
| 18 | 3-nitrophenyl | 3-nitrobenzyl bromide | 5.5 | D, M | 249–251 |
| 19 | 2-methylphenyl | 2-methylbenzyl chloride | 5 | M | 241–242 |
| 20 | 3-methylphenyl | 3-methylbenzyl chloride | 6 | M | 223 |
| 21 | 4-methylphenyl | α-chloro-p-xylene | 2 | M | 213–214 |
| 22 | 2,4-dimethylphenyl | 2,4-dimethylbenzyl chloride[f] | 5 | M | 243–245 |
| 23 | 2,5-dimethylphenyl | 2,5-dimethylbenzyl chloride | 4 | M[g] | 269–271 |
| 24 | 2,6-dimethylphenyl | 2,6-dimethylbenzyl chloride[h] | 3.5 | D, M | 287–290 |
| 25 | 3,4-dimethylphenyl | 3,4-dimethylbenzyl chloride[aa] | 5 | A | 216–218 |
| 26 | 3,5-dimethylphenyl | 3,5-dimethylbenzyl chloride[i] | 3.3 | M | 261.5–263.0 |
| 27 | 2,4,6-trimethylphenyl | 2,4,6-trimethylbenzyl chloride | 4 | M | 256 |
| 28 | 2,3,5,6-tetramethylphenyl | 2,3,5,6-tetramethylbenzyl chloride | 3 | D | 281–282 |
| 29 | 4-isopropylphenyl | 4-isopropylbenzyl chloride[j] | 5 | A | 230–232 |
| 30 | 4-t-butylphenyl | 4-t-butylbenzyl chloride | 4 | M, A | 279–280 |
| 31 | 4-(methylthio)phenyl | 4-(methylthio)benzyl chloride[k] | 21 | A | 217–221 |
| 32 | 2-methoxyphenyl | 2-methoxybenzyl chloride[l] | 4 | M | 213–216 |
| 33 | 3-methoxyphenyl | 3-methoxybenzyl chlorine[m] | 4 | M | 205–207 |
| 34 | 4-methoxyphenyl | 4-methoxybenzyl chloride | 4 | P, M-A, M | 205–206 |
| 35 | 2,3-dimethoxyphenyl | 2,3-dimethoxybenzyl chloride[n] | 3 | M | 205.0–207.5 |
| 36 | 2,5-dimethoxyphenyl | 2,5-dimethoxybenzyl chloride[o] | 3 | M | 228–230 |
| 37 | 3,4-dimethoxyphenyl | 3,4-dimethoxybenzyl chloride[bb] | 4 | M | 222–226 (softens 218) |
| 38 | 3,4-(methylenedioxy)phenyl | 3,4-(methlenedioxy)benzyl chloride[p] | 3.8 | M[q] | 235.5–237.5 |
| 39 | 3,4,5-trimethoxyphenyl | 3,4,5-trimethoxybenzyl chloride | 4 | M | 240–241 |
| 40 | 4-ethoxyphenyl | 4-ethoxybenzyl chloride[r] | 2 | B-A | 200.5–203.0 |
| 41 | 3-thienyl | 3-thenyl bromide[s] | 2 | M, A | 212–213 (softens 210) |

TABLE I-continued

7-(Substituted)-7-H-pyrrolo[3,2-f]quinazoline-1,3-diamines

| Example No. | R | Alkylating Agent | Reax. Time (hours) | Recryst. Solv.[a] | m.p., °C |
|---|---|---|---|---|---|
| 42 | 4-thiazolyl | 4-chloromethylthiazole hydrochloride[t] | 24 | M | 254–255 |
| 43 | 2-pyridinyl | 2-picolyl chloride, hydrochloride[t] | 2.5 | M, A-M, P, M | 223–224 |
| 44 | 3-pyridinyl | 3-picolyl chloride, hydrochloride[t] | 4 | M[u] | 227 |
| 45 | 4-pyridinyl | 4-picolyl chloride, hydrochloride[z] | 6 | P | 232–234 (dec) |
| 46 | benzo[b]thien-3-yl | 3-chloromethylbenzo[b]thiophene[v] | 3 | D | 277.5–278.0 |
| 47 | 1-naphthalenyl | 1-chloromethylnaphthalene | 6 | M | 259–261 (dec) |
| 48 | 2-naphthalenyl | 2-chloromethylnaphthalenyl | 4 | M, M-E | 300–330[w] (dec) (softens 250) |
| 49 | 2-methyl-1-naphthalenyl | 1-chloromethyl-2-methylnaphthalene | 5 | M | 279–281 (dec) |
| 50 | 2-quinolinyl | 2-chloromethylquinoline, hydrochloride[t] | 6 | M | 208 |
| 51 | 8-quinolinyl | 8-quinolinylmethyl bromide | 5 | M[x] | 220–221 |
| 52 | 3,5-dimethyl-4-isoxazolyl | 3,5-dimethyl-4-chloromethylisoxazole | 3.3 | M[d] | 270.5–271.5 |
| 53 | n-hexyl | n-heptyl bromide | 50 | P | 154 |
| 54 | cyclohexyl | bromomethylcyclohexane | 71 | E-B, E-P | 192[y] |
| 55 | 2-methyl-1-propenyl | 1-chloro-3-methyl-2-butene | 5 | A | z |
| 56 | 2-phenylethyl | 1-iodo-3-phenylpropane | 65 | M | 182–183 |
| 57 | 2-phenylvinyl | cinnamyl bromide | 3 | A | 224–226 |
| 58 | 3,5-dimethoxyphenyl | 3,5-dimethoxybenzyl chloride[cc] | 19 | M, A | 213–215.5 |
| 59 | 2-thienyl | 2-chloromethylthiophene[dd] | 2 | A | 203–205 |
| 60 | 1-bromo-2-naphthalenyl | 1-bromo-2(bromomethyl)- | 4 | M[ee] | 263.5–265.0 |

TABLE I-continued 7-(Substituted)-7-H-pyrrolo[3,2-f]quinazoline-1,3-diamines

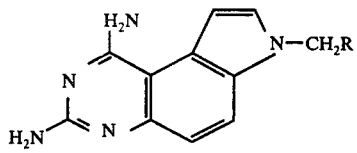

| Example No. | R | Alkylating Agent | Reax. Time (hours) | Recryst. Solv.[a] | m.p., °C |
|---|---|---|---|---|---|
| | | naphthalene | | | |

[a] A=acetone, B=acetonitrile, D=dimethylformamide, E=absolute ethanol, M=methanol, N=nitromethane, P=1-propanol, W=water;
[b] This compound is isolated as the hydrate bearing three-fourths molecule of water per molecule of diamine;
[c] This compound is isolated as the hydrate bearing one-third molecule of water per molecule of diamine and melts at 220–223°, but the melt is not completely clear until 270° at which temperature substantial decomposition has occurred.
[d] The crude product is thoroughly triturated with hot water prior to recrystallization;
[e] Addition of 4-bromoethylbenzoyl bromide in benzene to absolute ethanol-benzene, stirring for 1.5 hours, removal of solvent and distillation of the residue provide this bromide, b.p. 104–117°/2mm., m.p. 35–38° (cloudy). A. F. Titley [J. Chem. Soc., 1928, 2581] reported b.p. 165°/18 mm., m.p. 35–36°;
[f] This chloride, b.p. 91°/10 mm., is obtained by adding the corresponding alcohol in benzene to thionyl chloride-benzene-pyridine according to the method of Neuman [J. Am. Chem. Soc., 62, 2295 (1940)]. R. B. Akin et al., [J. Am. Chem. Soc., 59, 1268 (1937)] recorded b.p. 116–118°/16 mm. and 86–87°/7mm.
[g] The crude product is recrystallized twice from methanol, washed with 2:1 N sodium hydroxide-methanol, with water and dried prior to final recrystallization from methanol;
[h] The alcohol is converted by the method of Neuman (see footnote f) to the chloride, b.p. 75–77/2 mm. V. F. Raaen and J. F. Eastham [J. Am. Chem. Soc., 82, 1349 (1960) listed b.p. 75–80°/1 mm.;
[i] This halide, b.p. 103–104°/15 mm. is synthesized by the method of Neuman (see footnote f). B. van Zan'en et al., Rec. trav. chim., 79, 1211 (1960) [C.A., 55, 7403e (1961)] reported b.p. 100–110°/15 mm.;
[j] This compound contains ≦ 13% of the o-isopropyl isomer based on NMR examination. Chloromethylation of cumene according to the procedure of G. Blanc. [Bull. soc. shim. [4], 33, 317 (1933), also Org. Reactions, 1, 67] gives 4-isopropyl benzyl chloride containing ≦ 11% 2-isopropyl isomer (NMR evidence);
[k] The crude halide prepared by the procedure of R. F. Czaja et al., U. S. Pat. No. 3,953,520 is distilled twice to yield an oil, b.p. 93–96°/1 mm. which is 94% 4-methylthiobenzyl chloride by gas chromatographic assay. M.W. Goldberg and M. Janpulsky, U. S. Pat No. 2,624,738 recorded b.p. 83%/0.3 mm.;
[l] This chloride, b.p. 77–79°/2 mm., is prepared by the method of Z. Horii et al., Yakugaku Zasshi, 77, 252 (1957) [C.A., 51, 8671c (1957)] who reported b.p. 88–89°/4 mm.;
[m] This chloride, b.p. 70–74°/2 mm. is obtained by the procedure of Z. Horii et al., (see footnote l). J. W. Cornforth and R. Robinson (J. Chem. Soc., 1942, 686) reported b.p. 112–115%/10 mm.;
[n] This chloride, b.p. 103–104°/2 mm., is synthesized by the method of J. Harley-Mason and A. H. Jackson (J. Chem. Soc., 1954, 1165). A. Kaufmann and H. Muller, [Chem. Ber., 51, 123 (1918)] recorded b.p. 128.5–129.0/11 mm. (with decomposition);
[o] This chloride, m.p. 65–68° after recrystallization from hexane, is prepared by the procedure of J. Harley-Mason and A. H. Jackson (see footnote n) who reported m.p. 70–72°;
[p] This chloride, b.p. 93–95°/2 mm. is synthesized by the method of Z. Horii et al., (see footnote l). Spath and Schmitt, Monatsch. 53/54, 469 [Beilstein, 19, II, 21] recorded b.p. 89–91°/1 mm.;
[q] The crude product is recrystallized twice from methanol, stirred one hour with a solution of 3.00 g. sodium methoxide-350 ml. methanol, washed with water, dried and recrystallized from methanol;
[r] This chloride is synthesized by the method of Neuman (see footnote f), b.p. 96–103°/2-3 mm. A. L. Mndzhizan et al. [C.A., 55, 14466b (1961)] listed b.p. 102–105°/1 mm.;
[s] The directions of E. Campaign and B. F. Tullar (Org. Syn., Coll. Vol. IV, 921) are used and the twice-distilled, lachrymatory product (b.p. 59–67°/2-3 mm., ca. 6:4 mixture of 3-thenyl bromide and2-bromo-3-methylthiophene by gas chromatographic assay) is used directly in the alkylation reaction;
[t] 2.2 Molecules of sodium hydride per mole of substrate are used in this preparation in order to liberate the alkylating agent from its salt;
[u] The crude product is crystallized from methanol and converted to a salt with excess isopropanolic hydrogen chloride. Recrystallization of the salt from methanol is followed by regeneration of the base (with aqueous sodium hydroxide) and final recrystallization of the diamine from methanol;
[v] This halide, m.p. 38–40° after distillation (b.p. 139–141°/7 mm.) and recrystallization from pentane is prepared by the method of G. Wolf and F. Zymolkowski [Arch. Pharm., 309, 279 (1976)]. W. J. King and F. F. Nord [J. Org. Chem., 13, 635 (1948)] recorded b.p. 152–153°/11 mm. and m.p. 39–40°;
[w] This compound is isolated as a monohydrate;
[x] The crude diamine is recrystallized twice from methanol, thoroughly washed with N sodium hydroxide, with water, dried and finally recrystallized from methanol to yield the product as the hydrate bearing one-eighth molecule of water per molecule of diamine;
[y] This compound is isolated as the hydrate bearing one-eighth molecule of water per molecule of diamine;
[z] This product melts at 166–170°, resolidifies and remelts at 183–186°;
[aa] This chloride, b.p. 86–87/8 mm. is prepared by the method of Neuman (see footnote f), R. B. Herr et al., [J. Am. Chem. Soc., 79, 4229 (1957)] reported b.p. 95–96°/10 mm.;
[bb] This chloride, m.p. 51° (after trituration with ether-hexane) is prepared by the procedure of F. Binns et al., [J. Chem. Soc. [C], 1970, 1134] who reported m.p. 46–48°;
[cc] This chloride, m.p. 46–47.5° after recrystallization from hexane, was prepared as described by R. Adams, S. MacKenzie Jr. and S. Loewe, J. Am. Chem. Soc., 70, 664 (1948) who recorded m.p. 46°;
[dd] The chloride b.p. 77.0–77.5°/18–20 mm. was prepared according to the method recorded by Toyo Koatsu Industrial Inc., Jap. Pat. 9585 (1962); [C.A., 59, 3896b(1963)] who recorded b.p. 84–86°/20 mm.;
[ee] The crude product was dissolved in methanol and treated with sodium methylate before crystallization.

EXAMPLE 61

7-[(4-Acetylphenyl)methyl]-7H-pyrrolo[3,2-f]-quinazoline-1,3-diamine

Employing the procedure of H. B. Hass and M. L. Bender [J. Am. Chem. Soc., 71, 1767 (1949)] 54.43 g. of α-bromo-p-tolunitrile in 600 ml. benzene is reacted with 16.49 g. of sodium methoxide to provide 33.24 g. (4-cyanobenzyl)methyl ether, b.p. 114°–117°/5-6mm. (Hass and Bender reported b.p. 101°–102°/4 mm.).

To 5.93 g. methyl lithium in 300 ml. anhydrous ether is added a solution of 33.11 g. (4-cyanobenzyl)methyl ether in 150 ml. anhydrous ether and the reaction mixture is refluxed for 5 hours. After cooling, the reaction mixture is poured into 500 ml. of 20% w/v ammonium chloride solution, shaken and the organic layer separated. The aqueous phase is extracted with ether and the combined organic fractions are washed with brine, dried (sodium sulfate) and freed of solvent. The residue is stirred with 300 ml. N hydrochloric acid for one day and allowed to stand at ca. 25° for two days. Water (350 ml.) is added and the product is extracted into ether. After washing with brine, the ethereal extracts are dried (sodium sulfate) and freed of solvent. Distillation of the residue yields 23.5 g. (4-acetylbenzyl)methyl ether, b.p. 97°–104°/1-2mm. [Hass and Bender, J. Am. Chem. Soc., 71, 1767 (1949) reported b.p. 107°–109°/3.5 mm.].

The above (4-acetylbenzyl)methyl ether (23.44 g.) is refluxed 2 hours with 50 ml. 48% hydrobromic acid. Dilution of the reaction mixture with 150 ml. water is followed by extraction of the product into ether and the extracts are washed with brine and dried (sodium sulfate). Solvent is removed and the residue is distilled. The product, b.p. 106°–122°/1 mm., upon standing for 5 days partially solidifies. The minor liquid phase is removed by decantation and the solid fraction is redistilled thereby affording 16.24 g. 4-acetylbenzyl bromide, b.p. 108°–116°/2 mm. [Hass and Bender, J. Am. Chem. Soc., ibid. recorded b.p. 134°–136°/5 mm.].

In a manner similar to that of Example 2, 7.97 g. 7-H-pyrrolo[3,2-f]quinazoline-1,3-diamine in 350 ml. dry dimethylformamide is converted to the Nind-sodium salt with 2.31 g. ca. 50% sodium hydride-mineral oil dispersion and the salt is treated with 4-acetylbenzyl bromide (10.23 g.) in 10 ml. dry dimethylformamide. After stirring for 3 hours, the reaction mixture is treated with 5 ml. gl. acetic acid and freed of solvent. The residue is stirred with excess aqueous potassium carbonate solution, washed with water, with ether, and dried. Two recrystallizations of the crude product from methanol and thorough drying provide 9.82 g. of title compound, m.p. 224°–225°.

EXAMPLE 62

7-[(3-Aminophenyl)methyl]-7H-pyrrolo[3,2-f]quinazoline-1,3-diamine

A mixture of 7.3 g. 7-[(3-nitrophenyl)methyl]-7H-pyrrolo[3,2-f]-quinazoline-1,3-diamine in 500 ml. gl. acetic acid and 0.7 g. 10% palladium-carbon catalyst is hydrogenated at atmospheric pressure and ca. 25°. After ca. 2.5 hours, hydrogen absorption ceases and the reaction mixture is filtered. The filtrate is freed of solvent and the residue is stirred in excess aqueous potassium carbonate solution, collected, washed with water and dried. This material is recrystallized (twice) from methanol and dried to yield 3.55 g. triamine.

A solution of triamine (3.4 g.) in 50 ml. N hydrochloric acid is diluted with 100 ml. acetone and chilled. The salt that separates is washed with acetone and dried to yield the title compound as the dihydrochloride, monohydrate, salt, dec. 328°.

Analysis for: $C_{17}H_{16}N_6 \cdot 2HCl \cdot H_2O$: Calculated: C, 51.65; H, 5.10; Cl, 17.94; N, 21.26. Found: C, 51.40; H, 4.77; Cl, 18.22; N, 21.17.

EXAMPLE 63

7-[(4-Methylsulfonylphenyl)methyl]-7H-pyrrolo[3,2-f]quinazoline-1,3-diamine

A solution of 56.0 g. 4-methylsulfonyltoluene in 2 l. benzene (made anhydrous by distillation of ca. 300 ml. solvent) is cooled to ca. 25° C. and is treated with 57.5 g. N-bromosuccinimide and then with 5 g. benzoyl peroxide. The solution is refluxed 1.5 hours and then is allowed to stand at ca. 25° for 16 hours. After removal of the crystalline solid by filtration, the filtrate is freed of solvent, and the residual oil is dissolved in methanol. Thorough chilling of the methanolic solution gives a crystalline product which is recrystallized from methanol to yield 21.0 g. (4-methylsulfonyl)benzyl bromide, m.p. 94°–95° [D. A. A. Kidd and D. E. Wright (J. Chem. Soc., 1962, 1420) prepared this compound by a similar method and reported m.p. 93°–94°].

In a manner similar to that of Example 2, 3.98 g. 7H-pyrrolo[3,2-f]quinazoline-1,3-diamine in ca. 250 ml. dry dimethylformamide are reacted with 1.06 g. ca. 50% sodium hydride-mineral oil dispersion and then with 5.48 g. (4-methylsulfonyl)benzyl bromide for 6 hours. The crude product is recrystallized (twice) from methanol to afford 4.82 g. title compound, m.p. 248°

EXAMPLE 64

7-[(4-Trifluoromethoxyphenyl)methyl]-7H-pyrrolo[3,2-f]quinazoline-1,3-diamine

A solution of 20.16 g. 4-trifluoromethoxybenzoic acid in 160 ml. dry tetrahydrofuran is added dropwise to a stirred suspension of 4.61 g. lithium aluminum hydride in 160 ml. dry tetrahydrofuran. The mixture then is refluxed for 3.5 hours, cooled and 25 ml. N sodium hydroxide is added cautiously. After stirring for 0.5 hours, the reaction mixture is filtered and the insolubles are thoroughly washed with hot tetrahydrofuran. The tetrahydrofuran fractions are freed of solvent and the residue is distilled to yield 15.82 g. (4-trifluoromethoxy)benzyl alcohol, b.p. 98°–99°/9–10 mm. [W. A. Sheppard, J. Org. Chem., 29, 1 (1964) reported b.p. 108°/25 mm.].

A solution of 15.72 g. (4-trifluoromethoxy)benzyl alcohol in 170 ml. thionyl chloride is refluxed for 14 hours and excess thionyl chloride is removed in vacuo. Distillation of the residue yields 7.96 g. (4-trifluoromethoxy)benzyl chloride, b.p. 70°–74°/11–15 mm.

Analysis for: $C_8H_6F_3ClO$: Calculated: C, 45.62; H, 2.87. Found: C, 45.66; H, 2.87.

A solution of 4.98 g. 7H-pyrrolo[3,2-f]quinazoline-1,3-diamine in 250 ml dry dimethylformamide is stirred with 1.32 g. ca. 50% sodium hydride-mineral oil disperson for 1.5 hours and then a solution of 5.79 g. (4-trifluoromethoxy)-benzyl chloride in 10 ml. dry dimethylformamide is added. After stirring 3.5 hours at room ca. 25°, 40 ml. gl. acetic acid are added and stirring is continued for 15 min. Solvent is removed in vacuo and the residue is stirred with excess aqueous potassium carbonate, washed with water, with ether, and dried. Two recrystallizations of the crude product from methanol yield 7.56 g. title compound, m.p. 205.0°–207.5°.

EXAMPLE 65

7-Methyl-7H-pyrrolo[3,2-f]quinazoline-1,3-diamine

A solution of 5.98 g. 7H-pyrrolo[3,2-f]quinazoline-1,3-diamine in 200 ml. dry dimethylformamide is stirred under nitrogen and 1.58 g. ca. 50% sodium hydride-mineral oil dispersion is added carefully. After stirring for one hour, a solution of 4.47 g. (2.0 ml.) methyl iodide in 10 ml. dry dimethylformamide is added and stirring is continued. Two hours later, 15 ml. gl. acetic acid are added and the reaction mixture is freed of solvent (in vacuo). The residue is stirred with excess aqueous potassium carbonate solution for several hours and the solids are collected, washed with water and dried. A solution of this crude product in 200 ml. water-10 ml. gl. acetic acid is washed with ether. Basification of the acidic solution gives a precipitate that is washed with water and then is crystallized from methanol-acetone to yield 3.44 g. title compound as a hydrate bearing one-third molecule of water per molecule of diamine, m.p. 250°; NMR (dDMSO): δ 3.88 (singlet, 7-CH$_3$), 7.02 (doublet, J=3Hz, 9H), 7.15 (doublet, J=9Hz, 5 or 6H), 7.41 (doublet, J=3Hz, 8H), 7.72 (doublet, J=9Hz, 5 or 6H) p.p.m.; $\lambda_{max}^{95\% \ EtOH}$ 234 (ε 25,280), 258 (ε 24,540), 317 (ε 9,090), 345 sh (ε 7,810) nm; $\lambda_{min}^{95\% \ EtOH}$ 243 (ε 23,570), 280 (ε 2,040)nm.

A solution of 3.32 g. of 7-methyl-7H-pyrrolo[3,2-f]-quinazoline-1,3-diamine in 50 ml. ethanol is treated with 3 ml. of gl. acetic acid. Addition of 250 ml. ether gives a precipitate that is recrystallized from methanolethanol to yield 3.07 g. title compound as the monoacetate salt, m.p. 247°-249° (dec.).

EXAMPLE 66

7-(3-Methylbutyl)-7H-pyrrolo[3,2-f]quinazoline-1,3-diamine

In a manner similar to that of Example 2, 3.98 g. 7H-pyrrolo[3,2-f]quinazoline-1,3-diamine in ca. 210 ml. dry dimethylformamide are reacted with 1.06 g. ca. 50% sodium hydride-mineral oil dispersion and then with 4.06 g. 1-iodo-3-methylbutane. The reaction time is four hours. The crude product is recrystallized from acetone and from acetone-methylene chloride to yield 2.58 g. diamine, m.p. 185°-195° (softens 180°).

A solution of 2.5 g. preceding diamine is dissolved in 100 ml. N hydrochloric acid-400 ml. methanol and the solution is concentrated to a volume of ca. 100 ml. and chilled. The salt that separates is recrystallized from methanol-ethanol to provide 1.70 g. title compound as a monohydrochloride, hemihydrate salt, m.p. 300° (dec.).

EXAMPLE 67

7-[(Tetrahydro-2-furanyl)methyl]-7H-pyrrolo-[3,2-f]quinazoline-1,3-diamine

In a manner similar to that of Example 2, 3.98 g. of 7H-pyrrolo[3,2-f]quinazoline-1,3-diamine in ca. 260 ml. dry dimethylformamide are reacted with 1.06 g. ca. 50% sodium hydride-mineral oil dispersion and then with 3.63 g. tetrahydrofurfuryl bromide. After stirring the mixture at ca. 25° for 24 hours, 0.21 g. ca. 50% sodium hydride-mineral oil dispersion are added. Stirring is continued for one-hour, 0.73 g. tetrahydrofurfuryl bromide is added, and, after stirring for 6 hours, the reaction mixture is kept at ca. 25° for ca. 70 hours. Processing of the reaction mixture in the manner described in Example 2 (Method A) yields a brown gum which is dissolved in 40 ml. N hydrochloric acid. Dilution of the aqueous acidic solution with 40 ml. acetone gives crystals that are collected and twice recrystallized from methanol-acetone to yield 1.20 g. title compound as a monohydrochloride salt bearing one-third molecule of water per molecule of diamine salt, m.p. 310°-311° (dec.).

Analysis for: $C_{15}H_{17}N_5O.HCl.\frac{1}{3}H_2O$: Calculated: C, 55.30; H, 5.77; Cl, 10.88; N, 21.50. Found: C, 55.32; H, 5.65; Cl, 10.85; N, 21.85.

EXAMPLE 68

7-(4-Carboxybenzyl)-7H-pyrrolo[3,2-f]-quinazoline-1,3-diamine, sodium salt

A suspension of 3.98 g. 7H-pyrrolo[3,2-f]quinazoline-1,3-diamine (20 mmoles) in 350 ml. dry dimethylformamide is stirred (under nitrogen) with 2.11 g. ca. 50% sodium hydride-mineral oil dispersion (44 mmoles) for 1.5 hours. 4-Bromomethyl benzoic acid (4.73 g., 22 mmoles) is added, and stirring is continued for 5 hours and the mixture is allowed to stand at ca. 25° overnight. The solvent is removed (in vacuo) and the residue is dissolved in 200 ml. water. After washing with chloroform and filtration, the aqueous solution is adjusted to pH ca. 4 with acetic acid and permitted to stand overnight. The solids are collected, washed with water and dried. Recrystallization of the crude product from acetic acid and washing with methanol is carried out twice. Dissolution of the resulting solid in dilute aqueous sodium hydroxide and acidification of the aqueous solution to pH ca. 5 with acetic acid yields a product which is washed with water and dried. This material (2.5 g.) is dissolved in 70 ml. N sodium hydroxide and the solution is filtered. Upon standing, a salt separates which is collected, washed with acetone, recrystallized from methanol and dried to yield 1.31 g. title compound as the hydrate, bearing one-fourth molecule of water per molecule of sodium salt, m.p. > 360°.

Analysis for: $C_{18}H_{15}N_5O_2Na.0.25\ H_2O$: Calculated: C, 60.08; H, 4.06; N, 19.46. Found: C, 59.94; H, 3.88; N, 19.44.

EXAMPLE 69

7-(4-Cyanophenyl)-7H-pyrrolo[3,2-f]-quinazoline-1,3-diamine

A solution of 15.94 g. 7H-pyrrolo[3,2-f]quinazoline-1,3-diamine in 800 ml. dry dimethylformamide is stirred, under nitrogen, with 4.61 g. ca. 50% sodium hydride-mineral oil dispersion for 1.5 hours. Addition of 10.66 g. 4-fluorobenzonitrile is followed by heating of the reaction mixture at 95° for 6 hours. Glacial acetic acid (40 ml.) is added and the solvent is removed in vacuo. The residue is stirred thoroughly with excess aqueous potassium carbonate solution, collected, washed with water and dried. Two recrystallizations of the crude product from dimethylformamide, followed by washing with a small amount of dimethylformamide, with methanol and thorough drying, yield the title compound, m.p. 344° (dec.), NMR (dDMSO): δ 7.17 (doublet, J=9Hz, 5 or 6H), 7.42 (doublet, J=3Hz, 9H), 7.76-7.95 (four protons multiplet, 5 or 6H, 8H and two protons meta to the cyano group), 8.09 (two proton doublet, J=8Hz, two protons ortho to the cyano group) p.p.m.

EXAMPLES 70-95

Employing conditions similar to those recorded in Example 69, 7-H-pyrrolo[3,2-f]quinazoline-1,3-diamine, in dimethylformamide, is converted to the sodium salt with ca. 50% sodium hydride-mineral oil dispersion. The salt is treated with the indicated halide for the period and at the temperature noted to provide the 7-substituted-7H-pyrrolo[3,2-f]quinazoline-1,3-diamines described in Table II.

TABLE II 7-(Substituted)-7H-pyrrolo[3,2-f]quinazoline-1,3-diamines

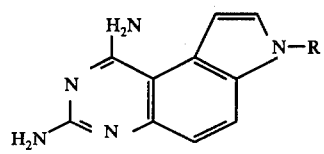

| Example No. | R | Alkylating Agent | Reax. Temp. (°C) | Reax. Time (hours) | Recryst. Solv.ᵃ | m.p., °C |
|---|---|---|---|---|---|---|
| 70 | 2-acetylphenyl | 2-fluoroacetophenon | 70 | 5 | M | 250-252 |

TABLE II-continued
7-(Substituted)-7H-pyrrolo[3,2-f]quinazoline-1,3-diamines

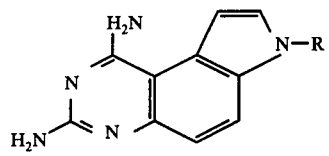

| Example No. | R | Alkylating Agent | Reax. Temp. (° C) | Reax. Time (hours) | Recryst. Solv.[a] | m.p., ° C |
|---|---|---|---|---|---|---|
| 71 | 4-acetylphenyl | 4-fluoroacetophenone | 65–70 | 13 | D | 290 |
| 72 | 4-propionylphenyl | 4-fluoropropiophenone | 80 | 6 | M, D | 262–264 (dec) |
| 73 | 2-cyanophenyl | 2-fluorobenzonitrile | 80 | 5 | D-A, M | 317–319 (dec) |
| 74 | 4-(methylsulfonyl)-phenyl | 4-(methylsulfonyl)fluorobenzene | 75 | 5 | D | 309–310 (dec) |
| 75 | 4-carbethoxyphenyl | ethyl 4-fluorobenzoate | 65 | 5 | M, D | 232 |
| 76 | 2-nitrophenyl | 2-fluoronitrobenzene | 90 | 5 | M | 296–299 (dec) |
| 77 | 4-nitrophenyl | 4-fluoronitrobenzene | 70 | 5 | D[b] | >340 |
| 78 | 2,4-dinitrophenyl | 2,4-dinitrofluorobenzene- | 80 | 5 | D[c] | 335 (dec) |
| 79 | 2-cyano-4-nitrophenyl | 2-chloro-5-nitrobenzonitrile | 95 | 6 | D | 343 (dec) |
| 80 | 3-methyl-4-nitrophenyl | 5-fluoro-2-nitrotoluene | 85–90 | 4 | M | 267 (dec)[d] |
| 81 | 2-thiazolyl | 2-bromothiazole | 110 | 4 | D, M[e] | 250 |
| 82 | 5-nitro-2-pyridinyl | 2-chloro-5-nitropyridine | 65 | 14 | D | 340 (dec) |
| 83 | 2-pyridinyl | 2-fluoropyridine | 110 | 6 | M[f] | 264–265 (dec) |
| 84 | 2-pyrimidinyl | 2-chloropyrimidine | 100 | 3.5 | D | 314–315 (dec) |
| 85 | 2-pyrazinyl | 2-chloropyrazine | 94 | 6 | D | 283–284 |
| 86 | 2-quinolinyl | 2-chloroquinoline | 75 | 12 | M | 270–272 |
| 87 | 4-quinolinyl | 4-chloroquinoline | 95 | 6 | D | 286–287 |
| 88 | 4-methyl-2-quinolinyl | 4-chlorolepidine | 100 | 10 | D | 257–258 |
| 89 | 7-chloro-4-quinolinyl | 4,7-dichloroquinoline | 96 | 6 | D | 319–320 (dec) |
| 90 | 7-trifluoromethyl-4-quinolinyl | 4-chloro-7-(trifluoromethyl)quinoline | 95 | 6 | M[g] | 283 |
| 91 | 2-methyl-4-quinolinyl | 4-chloroquinaldine | 105 | 6 | B[h] | 265 |
| 92 | 3-methyl-2-quinoxalinyl | 2-chloro-3-methylquinoxaline | 104 | 6 | D, M | 298–299 (dec) |
| 93 | 2-trifluoromethylphenyl | 2-fluorobenzotrifluoride | 110 | 6 | A[f] | 236–237 |
| 94 | 2-trifluoromethyl-4-nitrophenyl | 2-fluoro-5-nitrobenzotrifluoride | 110 | 6 | M[g] | 319–320 |
| 95 | 2-phenyl-4-quinolinyl | 4-chloro-2-phenylquinoline | 110 | 5 | M[g] | 190–195[i] |

[a]A=acetone, B=acetonitrile, D=dimethylformamide, M=methanol;
[b]The product is triturated with methanol after recrystallization;
[c]The crude product is triturated with boiling acetone and with boiling methanol prior to recrystallization;
[d]This compound is isolated as the hydrate bearing two-thirds of a molecule of water per molecule of diamine;
[e]The crude product is thoroughly triturated with boiling water. The insoluble solids and the solids isolated from the aqueous triturate upon cooling to room temperature are combined and recrystallized;
[f]The crude product is thoroughly triturated with boiling water prior to recrystallization;
[g]This compound is isolated as the hydrate bearing one-fourth molecule of water per molecule of diamine;
[h]The crude product is triturated with boiling acetone prior to recrystalization; and
[i]Compound starts gasing at 170°.

EXAMPLE 96

7-(4-Aminophenyl)-7H-pyrrolo[3,2-f]-quinazaline-1,3-diamine

A mixture of 3.20 g. 7-(4-nitrophenyl)-7H-pyrrolo-[2,3-f]quinazoline-1,3-diamine, 200 ml. gl. acetic acid and 0.5 g. 10% palladium-carbon catalyst is hydrogenated at atmospheric pressure and ca. 25°. After about 1.25 hours, hydrogen absorption ceases, the mixture is filtered and the filtrate is freed of solvent. The residue is recrystallized (twice) from water and then is stirred with aqueous potassium carbonate solution. Washing of the precipitate thus formed with water and drying is followed by recrystallization from acetone thereby providing 1.48 g. title compound, dec. 180°–185° (softens 140°) as the hydrate bearing one-fourth molecule of water per molecule of triamine.

Analysis for: $C_{16}H_{14}N_6O \cdot 0.25 H_2O$: Calculated: C, 65.18; H, 4.96; N, 28.51. Found: C, 65.34; H, 4.92; N, 28.37.

EXAMPLE 97

7-(2-Benzothiazolyl)-7H-pyrrolo-[3,2-f]quinazoline-1,3-diamine

To 3.98 g. 7H-pyrrolo[3,2-f]quinazoline-1,3-diamine dissolved in 250 ml. dry dimethylformamide are added, with stirring under nitrogen, 1.15 g. ca. 50% sodium hydride-mineral oil dispersion. After stirring for 1.5 hours, 3.90 g. 2-chlorobenzothiazole are added and the mixture is heated at 95° for 3 hours. An additional 1.29 g. 2-chlorobenzothiazole are added and heating at 95° is continued for 11 hours. A third portion of 2-chlorobenzothiazole (1.29 g.) is added and heating at 95° is continued for 8 hours. The reaction mixture is processed as in Example 69 and the crude product is recrystallized (twice) from dimethylformamide and is thoroughly dried to yield 2.30 g. title compound, m.p. 326° (dec).

EXAMPLE 98

8-Methyl-7H-pyrrolo[3,2-f]quinazoline-1,3-diamine (a) To a thoroughly cooled and stirred solution of 52.47 g. 2-methylindole in 320 ml. conc. sulfuric acid is added 34.00 g. sodium nitrate during a period of 65 minutes keeping the reaction temperature at 0°–5°. After stirring 10 minutes longer, the reaction mass is poured into 3 Kg. ice and, ca. 20 minutes later, the yellow solids are collected, thoroughly washed with water and dried. The crude product, in ca. 3 l. chloroform is flushed thru a 1 Kg. column of neutral activity III alumina. Removal of solvent from the chloroform eluates and drying of the solids provide 57.2 g. 2-methyl-5-nitroindole, m.p. 169°–172° (softens 162°). [W. E. Noland et al., J. Org. Chem., 28, 2262 (1963) prepared this compound by a similar procedure and reported m.p. 176.0°–176.5°].

(b) To Grace No. 28 Raney nickel catalyst (8.8 g. wet weight, after thorough washing with water and with absolute ethanol) in 30 ml. absolute ethanol is added a solution of 8.81 g. 2-methyl-5-nitroindole in 140 ml. warm absolute ethanol. The mixture is hydrogenated in a Parr apparatus at ca. 3 atmospheres pressure and ca. 29°. Hydrogen absorption ceases in about 1 hour and the catalyst is removed by filtration through a Celite bed. The cake is washed thoroughly with boiling ethanol and the combined ethanolic fractions are freed of solvent. Recrystallization of the crude product from ethanol-water yields 5.55 g. 5-amino-2-methylindole as a mauve solid, m.p. 151.5°–154.5°. [W. E. Noland et al., J. Org. Chem., 28, 2262 (1963) prepared this compound similarly and recorded m.p. 157°–159°].

A solution of 5.44 g. of the above amine in 50 ml. methanol is cooled in an ice-water bath and is treated with excess isopropanolic hydrogen chloride and then with 150 ml. anhydrous ether. After chilling the resulting mixture for ca. 10 min. at 0°, the salt is collected, washed with ether and dried. Recrystallization of the salt from methanol (acidified with several drops isopropanolic hydrogen chloride)-ether and thorough drying afford 3.82 g. 5-amino-2-methylindole hydrochloride, dec. 280°–289° (darkens 268°).

(c) A mixture of 23.75 g. 5-amino-2-methylindole, hydrochloride, 28.94 g. sodium dicyanamide (previously recrystallized from methanol) and 800 ml. 1-octanol is heated to reflux, ca. 100 ml. solvent is distilled (b.p. ca. 196°) to insure anhydrous conditions, and the mixture is refluxed for 21 hours with stirring. The hot reaction mixture is filtered and the insolubles are washed with boiling 1-octanol. The octanolic fractions are combined, cooled to ca. 25°, acidified with excess isopropanolic hydrogen chloride and diluted with ca. 2 l. anhydrous ether. After standing ca. 1.5 hours, the solids are collected, washed with anhydrous ether, triturated (twice) with ca. 100 ml. cold methanol, washed with ether and dried. The crude hydrochloride is dissolved in 400 ml. water-50 ml. N hydrochloric acid, filtered and the acidic solution is washed with ether, chilled and basified with excess aqueous sodium hydroxide solution. A yellow-brown solid separates from the basic solution and is collected, washed with water, dried and recrystallized from methanol to provide 11.68 g. buff solid. A 4.08 g. portion of this diamine is recrystallized from methanol to yield 3.67 g. title compound, dec. 324°–327°, NMR (dDMSO): δ 2.48 (singlet, 8-$CH_3$), 6.88 (singlet, 9H), 7.15 (doublet, J=9Hz, 5 or 6 H), 7.68 (doublet, J=9Hz, 5 or 6 H), 11.38 (broad singlet, exchangeable) p.p.m.; $\lambda_{max}^{95\% \ EtOH}$ 233 (ε 26,880), 264 (ε 19,640), 328 ε 8,740), 352 (ε 9,110) nm; $\lambda_{min}^{95\% \ EtOH}$ 255 (ε 18,570), 285.5 (ε 1,720), 335 (ε 8,680) nm.

Analysis for: $C_{11}H_{11}N_5$: Calculated: C, 61.95; H, 5.20; N, 32.85. Found: C, 61.72; H, 5.11; N, 32.86.

EXAMPLES 99–103

In a manner similar to that recorded in Example 2, (Method A) 8-methyl-7H-pyrrolo[3,2-f]quinazoline-1,3-diamine, in dimethylformamide, is converted to the Nind-sodium salt with ca. 50% sodium hydride-mineral oil dispersion and the salt is treated with the indicated halide for the specified period to afford the 7-(substituted)8-methyl-7H-pyrrolo-[3,2-f]quinazoline-1,3-diamines described in Table III.

TABLE III 7-(Substituted)-8-methyl-7H-pyrrolo[3,2-f]quinazoline-1,3-diamines

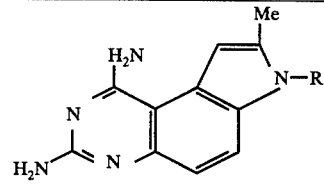

| Example No. | R | Alkylating Agent | Reax. Time (hours) | Recryst. Solv.$^a$ | m.p., ° C |
|---|---|---|---|---|---|
| 99 | meythyl | methyl iodide | 2 | M | 305–309 (dec) |
| 100 | benzyl | benzyl chloride | 19 | M | 267–270 |
| 101 | 3-cyanobenzyl | 3-cyanobenzyl bromide | 2 | $M^b$ | 277–280 (dec) |
| 102 | 4-cyanobenzyl | 4-cyanobenzyl bromide | 2 | $^c$ | 329–332 (dec) (softens 327) |
| 103 | 2,5-dimethylbenzyl | 2,5-dimethylbenzyl chloride | 18 | M, D | 308–311 (dec) |

$^a$M = methanol, D = dimethylformamide;
$^b$This reacton is conducted at 0° and the crude product is triturated (twice) with acetone prior to recrystallization;
$^c$This reaction is conducted at 0°. The crude product is recrystallized from dimethylformamide and the two crops of brown solid isolated are combined and extracted successively with boiling acetonitrile and with boiling methanol. Concentration and chilling of the combined acetonitrileand methanol extracts yields a buff solid which is finally recrystallized from methanol.

EXAMPLE 104

8-Chloro-7-(phenylmethyl)-7H-pyrrolo-[3,2-f]quinazoline-1,3-diamine (a) Nitration of 6.66 g. oxindole in 25 ml. conc. sulfuric acid with 2.1 ml. fuming nitric acid is conducted according to the procedure of W. C. Sumpter et al., J. Amer. Chem. Soc. 67, 499 (1945). Crystallization of the crude product from 50% acetic acid and from methanol yields 3.85 g. 5-nitrooxindole, m.p. 240°–242°. (Sumpter et al. recorded m.p. 240°–241°).

(b) Pyrrolidine (600 g.) and 110.0 g. 5-nitrooxindole are refluxed 1.5 hours and the dark solution is allowed to stand at ca. 25° overnight. The yellow crystals that separate are collected, washed with ether and dried to give 143 g. solid. A 20 g. portion is recrystallized from methanol thereby providing 1[(2-amino-5-nitrophenyl)acetyl]pyrrolidine, m.p. 210°–211°

(c) Benzaldehyde (51.16 g.) and 10.0 g. 1-[(2-amino-5-nitrophenyl)acetyl]pyrrolidine are combined and heated under a short distillation column for ca. 10 min. During this period the distillation temperature rises from 100° to 176° and approximately 15 ml. of distillate are collected. The reaction mixture then is cooled, poured into 700 ml. anhydrous ether and chilled. Recrystallization (methanol) of the solids that separate gives 9.70 g. 1-[[5-nitro-2-[(phenylmethylene)amino]phenyl]acetyl]pyrrolidine, m.p. 170°–171°.

(d) A solution of 16.0 g. 1-[[5-nitro-2-[(phenylmethylene)amino]phenyl]acetyl]pyrrolidine in 400 ml. hot methanol is stirred under nitrogen and 16.0 g. sodium borohydride are added in portions during ca. 20 min. such that refluxing is maintained. The reaction mixture is refluxed an additional 20 minutes and then is diluted with an equal volume of water. A yellow precipitate forms and the solid is collected, dried, recrystallized from methanol and dried to provide 13.2 g. 1-[[5-nitro-2-[(phenylmethyl)amino]phenyl]acetyl]pyrrolidine, m.p. 128°–129° as the hydrate bearing one-eighth molecule of water per molecule aminoamide.

Analysis for: $C_{19}H_{21}N_3O_3 \cdot 0.125\ H_2O$: Calculated: C, 66.79; H, 6.27; N, 12.30. Found: C, 66.72; H, 6.36; N, 12.29.

(e) Acetic acid (2.5 l.), 500 ml. N hydrochloric acid and 90.0 g. 1-[[5-nitro-2-[(phenylmethyl)amino]phenyl]acetyl]pyrrolidine are refluxed three hours and the reaction mass is concentrated (in vacuo) to a volume of ca. 0.5 l. and cooled. The yellow solid is collected and dried to afford 67.3 g. solid, m.p. 137°–138°. A 5.0 g. portion is recrystallized from methanol and dried to provide 3.50 g. 1-benzyl-5-nitrooxindole, m.p. 143°–144°; NMR (dDMSO): δ 3.83 (two proton singlet, 3H, 3H), 4.97 (two proton singlet, —N—CH$_2$—), 7.10 (doublet, J=9Hz, 7H-), 7.33 (five proton singlet, phenyl protons), 8.17 (two proton singlet, 4 and 6 protons) p.p.m.

(f) Phosphorus oxychloride (100 ml.), 5 ml. pyridine and 10.0 g. 1-benzyl-5-nitrooxindole are refluxed 3 hours and the reaction mass concentrated in vacuo (in hood) to a gum which is dissolved in 500 ml. chloroform and stirred with 0.5 l. saturated aqueous sodium bicarbonate solutions for 4 hours. Adjustment of the pH to ca. 9 with potassium carbonate is followed by stirring for one hour. The organic phase is separated, washed with brine, dried (magnesium sulfate) and flushed thru a 500 g. column of neutral, activity III alumina. Removal of solvent from the chloroform eluates gives a solid which is dried to produce 9.1 g. 1-benzyl-2-chloro-5-nitroindole, m.p. 106°–107°, NMR (CDCl$_3$): δ 5.40 (two proton singlet, —N—CH$_2$—), 6.68 (singlet, 3H), 6.98–7.36 (six proton multiplet, phenyl proton and 7H), 8.00 (doublet of doublet, J=9Hz, J=2Hz, 6H), 8.42 (doublet, J-2Hz, 4H) p.p.m.

(g) A refluxing and stirred solution of 25.7 g. 1-benzyl-2-chloro-5-nitrooxindole in 600 ml. methanol and 180 ml. toluene is treated with a solution of 45 g. commercial NaSH (xH$_2$O) in 320 ml. methanol during a period of 10 minutes and refluxing is continued. At subsequent intervals of ½ and one hour, the addition of NaSH (xH$_2$O) in methanol is repeated exactly and the reaction mixture is refluxed 2.5 hours longer. Following filtration, the organic solution is freed of solvent and the residue is throughly washed with water and dried. The resulting solid (19.7 g.) is dissolved in 200 ml. acetone and the solution is acidified with excess isopropanolic hydrogen chloride and diluted with 1 l. anhydrous ether. A gum forms which is separated by decantation, thoroughly triturated with acetone and dried to afford 16.1 g. 5-amino-1-benzyl-2-chloroindole, hydrochloride, m.p. 228° (dec).

Analysis for: $C_{15}H_{13}ClN_2 \cdot HCl$: Calculated: C, 61.44; H, 4.81; Cl, 24.19; N, 9.56. Found: C, 61.16; H, 4.71; Cl, 23.78; N, 9.42.

(h) A mixture of 14.65 g. 5-amino-1-benzyl-2-chloroindole hydrochloride, 11.14 g. sodium dicyanamide (previously recrystallized from methanol) and 300 ml. 1-octanol is refluxed 3 hours and then is allowed to stand at room temperature overnight. A solid (A) is separated by filtration, mixed with 200 ml. hot methanol and 400 ml. water and added to the mixture. Filtration of the mass yields a solid which, after washing with ether, melts at 280°–283°.

The octanolic filtrate, from which solid A is removed, is diluted with 700 ml. anhydrous ether and acidified with excess isopropanolic hydrogen chloride. The salt that forms is recrystallized from methanol and then is stirred with 50 ml. methanol-100 ml. N sodium hydroxide. Crude diamine is collected and, after washing with water and drying, melts at 280°–283°. The solids melting at 280°–283° are combined, recrystallized from dimethylformamide, washed with methanol and thoroughly dried to give 4.26 g. title compound, m.p. 285°–286°.

Analysis for: $C_{17}H_{14}ClN_5$: Calculated: C, 63.06; H, 4.36; Cl, 10.95; N, 21.62. Found: C, 62.89; H, 4.34; Cl, 10.84; N, 21.58.

EXAMPLE 105

8-Phenyl-7H-pyrrolo[3,2-f]-quinazoline-1,3-diamine (a) Nitration of 9.66 g. 2-phenylindole [previously purified by recrystallization from toluene and by dissolution in anhydrous ether, treating with charcoal, filtration, and removal of solvent, m.p. 184°–186° (softens 180°)] in 200 ml. concentrated sulfuric acid with a solution of 4.67 g. sodium nitrate in 100 ml. concentrated sulfuric acid is conducted in the manner reported by W. E. Noland et al., J. Org. Chem., 31, 65 (1966). The crude product is recrystallized from methanol thereby yielding 8.28 g. 5-nitro-2-phenylindole, m.p. 192°–194°. (Noland, et al., recorded m.p. 201°–203°).

(b) A mixture of 7.86 g. 5-nitro-2-phenylindole, 100 ml. absolute ethanol and 10 g. (wet weight) Grace No. 28 Raney nickel (previously washed with water and with absolute ethanol) is hydrogenated at ca. 3 atmospheres pressure and ca. 27° in a Parr apparatus. Hydrogen absorption ceases in ca. 3 hours and the reaction mixture, after dilution with ca. 300 ml. methylene chloride is filtered thru a Celite bed. The insolubles are washed with methylene chloride and with boiling ethanol. Removal of solvent from the combined organic solutions yields 6.51 g. 5-amino-2-phenylindole, m.p. 227°–229° (softens 217°), Noland et al., J. Org. Chem., 31, 65 (1966), prepared this amine similarly and reported m.p. 234°–235°.

Addition of excess isopropanolic hydrogen chloride to a solution of 6.42 g. 5-amino-2-phenylindole in 125 ml. methanol is followed by dilution with 700 ml. anhydrous ether and chilling. The salt that forms is collected, recrystallized from methanol (acidified with several drops isopropanolic hydrogen chloride)-ether and dried to give 4.98 g. amine hydrochloride. Recrystallization of a 1.1 g. portion in the same manner provide 0.82 g. 5-amino-2-phenylindole, hydrochloride, m.p. 314°–318° (dec., softens 280°).

Analysis for: $C_{14}H_{12}N_2 \cdot HCl$: Calculated: C, 68.71; H, 5.35; Cl, 14.49; N, 11.45. Found: C, 68.48; H, 5.32; Cl, 14.50; N, 11.49.

Sodium dicyanamide (22.26 g., previously recrystallized from methanol), 24.47 g. 5-amino-2-phenylindole hydrochloride and 700 ml. 1-octanol are heated to reflux with stirring, 100 ml. solvent are distilled to assure anhydrous conditions, and refluxing is continued for 3 hours. The hot reaction mixture is filtered and the insolubles are washed with boiling 1-octanol. The combined octanolic fractions, after cooling, are treated with 25 ml. concentrated hydrochloric acid and diluted with 3 l. acetone. After standing ca. 20 minutes the hydrochloride salt that separates is collected, washed with acetone and dried. A solution of the salt in ca. 800 ml. boiling water is filtered, cooled, and basified with aqueous sodium hydroxide solution. The brown base that forms is thoroughly washed with water, dried and crystallized from methanol to yield 14.98 g. diamine, m.p. 318°–319° (dec., softens 270°). Recrystallization of a 4.5 g. portion of this material from methanol and from acetone, followed by thorough drying yields 3.09 g. title compound, m.p. 322°–323° (dec., softens 320°).

Analysis for: $C_{16}H_{13}N_5$: Calculated: C, 69.80; H, 4.76; N, 25.44. Found: C, 69.85; H, 4.61; N, 25.51.

EXAMPLE 106

7-Methyl-8-phenyl-7H-pyrrolo[3,2-f]-quinazoline-1,3-diamine

In a manner similar to that recorded in Example 2 (Method A), 6.88 g. 8-phenyl-7H-pyrrolo[3,2-f]quinazoline-1,3-diamine in 300 ml. dry dimethylformamide is treated with 1.44 g. ca. 50% sodium hydride-mineral oil dispersion and the salt is reacted with 4.26 g. methyl iodide for 3 hours. The crude product is recrystallized from methanol (twice) and from acetonitrile to give 3.54 g. title compound, m.p. 295.0–296.5 (dec., softens 288°).

EXAMPLE 107

8,9,10,11-Tetrahydro-7H-pyrimido-[4,5-c]carbazole-1,3-diamine (a) To a partial solution of 91.88 g. (4-nitrophenyl)hydrazine in 1 l. boiling absolute ethanol are added, in turn, 58.88 g. cyclohexanone and 0.34 ml. glacial acetic acid. The deep brown-red solution is refluxed 1 hour and then is chilled thoroughly. The solid that separates is collected, washed with cold methanol and dried to yield 102 g. of the crystalline 4-nitrophenyl hydrazone of cyclohexanone, m.p. 143°–146°. Removal of solvent from the combined ethanolic-methanolic in liquor yields a slightly gummy solid which is recrystallized from methylene chloridehexane, washed with hexane and dried to afford an additional 20.8 g. hydrazone, m.p. 138°–141° (softens 133°). W. Borsche, A. Witte and W. Bothe [Ann., 359, 49 (1908); C.A., 2, 1716³ (1908)] recorded m.p. 146°–147° for this compound.

(b) The above hydrazone (122.6 g.) is carefully heated in 1.5 l. concentrated hydrochloric acid. Vigorous bubbling occurs as refluxing commences with separation of a brown solid in a few minutes. The mixture is refluxed 1 hour chilled and the solid is collected, washed with water, and dried. Recrystallization of the crude product from methanol and drying afford 92.1 g. 6-nitro-1,2,3,4-tetrahydrocarbazole, m.p. 171.5°–173.0° (softens 169°). D. S. Deorha and S. S. Joshi [J. Org. Chem., 26, 3527 (1961)] reported m.p. 177°.

(c) Hydrogenation of 43.25 g. 6-nitro-1,2,3,4-tetrahydrocarbazole in 750 ml. absolute ethanol with 50 g. (wet weight) Grace No. 28 Raney nickel in the manner described in Example 98, part b yields 36.1 g. light pink solid. This amine and a 26.7 g. quantity prepared in a similar experiment are combined and recrystallized from toluene to yield 55.95 g. 6-amino-1,2,3,4-tetrahydrocarbazole, m.p. 146°–150°. R. J. Brinton et al., J. Chem. Soc., 1956, 4783), prepared this tricyclic amine by Raney nickel-hydrazine reduction of 6-nitro-1,2,3,4-tetrahydrocarbazole and reported m.p. 151°–152°.

The above amine (55.80 g.) in 300 ml. methanol is acidified with excess isopropanolic hydrogen chloride and the solution is diluted with 2.6 l. anhydrous ether and chilled. The salt is collected, washed with ether, and dried to afford 61.82 g. 6-amino-1,2,3,4-tetrahydrocarbazole hydrochloride, m.p. 285°–288° (dec.).

(d) Sodium dicyanamide (71.23 g., previously recrystallized from methanol), 71.27 g. 6-amino-1,2,3,4-tetrahydrocarbazole hydrochloride and 2 l. 1-octanol are heated to reflux, ca. 230 ml. solvent is distilled to assure anhydrous conditions and refluxing is continued for 21 hours. The hot reaction mixture is filtered and the insolubles are washed with hot 1-octanol. Cooling of the combined octanolic fractions is followed by acidification with excess isopropanolic hydrogen chloride, dilution with ca. 2.6 l. anhydrous ether and chilling. The mustard-colored precipitate is collected, dried, triturated (twice) with 400 ml. portions cold methanol (acidified with few drops of isopropanolic hydrogen chloride), washed with ether, and dried. A suspension of the buff hydrochloride in 1.5 l. water is treated with excess aqueous sodium hydroxide solution and the mixture is vigorously stirred for ca. 1 hour. The base is collected, washed with water, dried, and recrystalized from methanol to give 24.66 g. buff diamine, m.p. 300°–303° (softens 297°). A 7.00 g. portion of base is recrystallized from methanol and dried to provide 6.17 g. title compound, m.p. 303°–306° (softens 285°), NMR (dDMSO): δ 1.67–1.97 (four proton multiplet, —CH₂CH₂CH₂CH₂—), 2.63–3.17 (four proton multiplet, —CH₂CH₂CH₂CH₂—), 6.92 (doublet, J=9Hz, 5 or 6H), 7.50 (doublet, J=9Hz, 5 or 6H), 11.07 (broad singlet, exchangeable, 7-H) p.p.m.

Analysis for: $C_{14}H_{15}N_5$: Calculated: C, 66.38; H, 5.97; N, 27.65. Found: C, 66.33; H, 5.94; N, 27.46.

EXAMPLE 108

8,9,10,11-Tetrahydro-7-(phenylmethyl)-7H-pyrimido[4,5-c]carbazole-1,3-diamine

Dry dimethylformamide (200 ml.), 6.33 g. 8,9,10,11-tetrahydro-7H-pyrimido[4,5-c]carbazole-1,3-diamine and 1.32 g. ca. 50% sodium hydride-mineral oil dispersion are stirred for ca. 1 hour. A solution of 3.48 g. benzyl chloride in 5 ml. dry dimethylformamide is added during ca. 5 minutes and stirring is continued for 19 hours. The reaction mixture is treated with 15 ml. glacial acetic acid, freed of solvent and the residue is stirred with excess aqueous potassium carbonate solution, washed with water, and dried. Two recrystallizations (methanol) of the solid residue yields, in two crops, 5.40 g. solid. To insure isolation of the diamine as the free base, 4.8 g. of this material in 60 ml. methanol are stirred with 1.37 g. sodium methoxide for 2 hours. Dilution of the suspension with 300 ml. water, washing of the precipitate with water and drying give a cream-colored diamine, m.p. 220°–223° (softens 218°). Recrystallization of the base from methanol affords 2.69 g. title compound, m.p. 223.5°–226.0° as the hydrate bearing one-fifth molecule of water per molecule of diamine.

Analysis for: $C_{21}H_{21}N_5 \cdot 0.20\ H_2O$: Calculated: C, 72.68; H, 6.22; N, 20.18. Found: C, 72.77; H, 6.24; N, 20.18.

EXAMPLE 109

8,9,10,11-Tetrahydro-7-methyl-7H-pyrimido[4,5-c]carbazole-1,3-diamine

Dry dimethylformamide (150 ml.), 4.62 g. 8,9,10,11-tetrahydro-7H-pyrimido[4,5-c]carbazole-1,3-diamine and 0.96 g. ca. 50% sodium hydride-mineral oil dispersion are stirred, under nitrogen, for 1 hour. A solution of 2.84 g. methyl iodide in 10 ml. dry dimethylformamide is added during 10 minutes and stirring is continued for ca. 2 hours. Glacial acetic acid (20 ml.) is added and the solvent is removed. The residue is stirred with 12 g. sodium methoxide-150 ml. methanol for 2 hours and the mixture is diluted with 750 ml. water. The solids are collected, washed with water, dried, twice recrystallized from methanol and thoroughly dried to yield 1.96 g. title compound, m.p. 288°-292° (softens 285°).

EXAMPLE 110

The ability of the compounds of Formula I to inhibit the growth of bacteria in vitro is demonstrated in the following test procedure:

A stock solution or suspension of the test compound at a concentration of 2500 μg/ml. is prepared utilizing a suitable solvent or medium such as aqueous sodium hydroxide, aqueous lactic acid, methyl cellosolve, dimethylsulfoxide, dimethylacetamide, ethylene glycol, dimethylformamide, formamide, propylene glycol, acetone or methanol. Two-fold dilutions are made by adding appropriate amounts of sterile water to the solution or suspension of the test substance. One ml. quantities of each dilution are incorporated into seed agar or Wellcotest Sensitivity Test Agar fortified with 5% hemolyzed horse blood (9 ml. vol.) in sterile Petri dishes to give plates containing varying concentrations of the test compound. The hardened surfaces of each plate are incubated with the test organism, and the plates are incubated for 18 hours at 35° C. The in vitro antibacterial activity of the compounds tested is expressed as the "minimal inhibitory concentration" (MIC) which is defined as the least amount of material (μg/ml.) that completely inhibits the test organism.

The in vitro antibacterial activities of compounds of the invention are set forth in Tables IV-VII below which sets forth the MIC values of various compounds when tested according to the above described procedure:

TABLE IV

In vitro Antibacterial Activity of 7-Substituted Methyl-7H-Pyrrolo[3,2-f]Quinazoline-1,3-Diamines

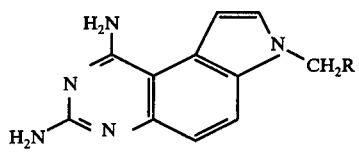

| Compound of Example | R | S. aureus Smith | S. aureus 53-180 | N. catarrhalis 8193 | E. coli 9637 | S. paratyphi 11737 | K. pneumoniae 10031 | P. vulgaris 6896 | Medium[a] |
|---|---|---|---|---|---|---|---|---|---|
| 2 | phenyl[b] | 1.95 | 1.95 | 0.061 | 1.95 | 1.95 | 1.95 | 7.81 | B |
| 3 | 2-fluorophenyl | 0.488 | 0.244 | 0.0152 | 0.488 | 0.976 | 0.122 | 0.976 | B |
| 4 | 3-fluorophenyl | 0.244 | 0.031 | <0.0009 | 0.244 | 0.488 | 0.061 | 0.488 | B |
| 5 | 4-fluorophenyl[c] | 0.244 | 0.122 | 0.0038 | 0.122 | 0.488 | 0.031 | 0.488 | B |
| 6 | 2-chlorophenyl | 0.976 | 0.976 | 0.061 | 0.976 | 1.95 | 0.976 | 7.81 | B |
| 7 | 3-chlorophenyl | 1.95 | 0.976 | 0.244 | 7.81 | 31.3 | 0.976 | 31.3 | B |
| 8 | 4-chlorophenyl | 0.976 | 0.244 | 0.0038 | 0.976 | 0.976 | 0.122 | 0.976 | B |
| 9 | 2,6-dichlorophenyl | 250 | 250 | 0.488 | >250 | >250 | 15.6 | >250 | B |
| 10 | 3,4-dichlorophenyl | 0.976 | 0.488 | 0.061 | 3.90 | 31.3 | 0.488 | 31.3 | B |
| 11 | 2-trifluoromethylphenyl | 0.488 | 0.244 | <0.0009 | 1.95 | 3.90 | 0.122 | 62.5 | B |
| 12 | 3-trifluoromethylphenyl | 0.488 | 0.244 | 0.122 | 0.976 | 7.81 | 0.488 | 62.5 | B |
| 13 | 4-trifluoromethylphenyl | 1.95 | 0.976 | 0.031 | 3.90 | 15.6 | 0.976 | 31.3 | B |
| 14 | 2-cyanophenyl | 0.244 | 0.244 | 0.061 | 0.244 | 0.488 | 0.122 | 1.95 | B |
| 15 | 3-cyanophenyl[d] | 0.061 | 0.031 | 0.0038 | 0.122 | 0.488 | 0.031 | 0.976 | B |
| 16 | 4-cyanophenyl | 0.244 | 0.122 | 0.0076 | 0.244 | 0.488 | 0.061 | 1.95 | B |
| 17 | 4-carbethoxyphenyl | 1.95 | 1.95 | 0.488 | 7.81 | >250 | 1.95 | >250 | B |
| 18 | 3-nitrophenyl[e] | 0.122 | 0.061 | 0.0152 | 0.488 | 0.976 | 0.122 | 3.90 | B |
| 19 | 2-methylphenyl | 0.488 | 0.488 | 0.0152 | 0.976 | 3.90 | 0.122 | 7.81 | B |
| 20 | 3-methylphenyl | 0.976 | 0.488 | 0.031 | 0.488 | 1.95 | 1.95 | 1.95 | B |
| 21 | 4-methylphenyl | 0.976 | 0.488 | 0.0152 | 0.976 | 1.95 | 0.122 | 1.95 | B |
| 22 | 2,4-dimethylphenyl | 0.244 | 0.244 | 0.0152 | 0.976 | 3.40 | 0.244 | 7.81 | B |
| 23 | 2,5-dimethylphenyl | 3.90 | 0.976 | 0.244 | 31.3 | 125 | 1.95 | 250 | B |
| 24 | 2,6-dimethylphenyl | 250 | 250 | 0.122 | 250 | >250 | 15.6 | >250 | B |
| 25 | 3,4-dimethylphenyl | 1.95 | 0.976 | 0.122 | 1.95 | 31.3 | 0.488 | 62.5 | B |
| 26 | 3,5-dimethylphenyl | 0.976 | 0.488 | 0.031 | 7.81 | 15.6 | 0.244 | 15.6 | B |
| 27 | 2,4,6-trimethylphenyl | 250 | 250 | 0.244 | >250 | >250 | 31.3 | >250 | B |
| 28 | 2,3,5,6-tetramethylphenyl | 15.6 | 15.6 | 0.244 | >250 | >250 | 3.90 | >250 | B |
| 29 | 4-isopropylphenyl | 1.95 | 0.976 | 0.244 | 7.81 | 62.5 | 0.488 | 62.5 | B |
| 30 | 4-t-butylphenyl | 7.81 | 3.90 | 0.976 | 250 | >250 | 3.90 | >250 | B |
| 31 | 4-(methylthio)phenyl | 0.976 | 0.488 | 0.0152 | 0.488 | 3.90 | 0.122 | 31.3 | B |
| 32 | 2-methoxyphenyl | 0.976 | 0.976 | 0.061 | 1.95 | 7.81 | 0.244 | 3.90 | B |
| 33 | 3-methoxyphenyl | 3.90 | 0.976 | 0.976 | 0.488 | 7.81 | 0.488 | 7.81 | B |

TABLE IV-continued

In vitro Antibacterial Activity of 7-Substituted Methyl-7H-Pyrrolo[3,2-f]Quinazoline-1,3-Diamines

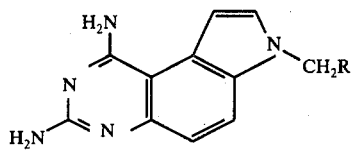

| Compound of Example | R | S. aureus Smith | S. aureus 53–180 | N. catarrhalis 8193 | E. coli 9637 | S. paratyphi 11737 | K. pneumoniae 10031 | P. vulgaris 6896 | Medium[a] |
|---|---|---|---|---|---|---|---|---|---|
| 34 | 4-methoxyphenyl | 0.976 | 0.244 | 0.0152 | 0.488 | 0.976 | 0.061 | 0.976 | B |
| 35 | 2,3-dimethoxyphenyl | 0.488 | 0.244 | 0.122 | 0.488 | 15.6 | 0.488 | 7.81 | B |
| 36 | 2,5-dimethoxyphenyl | 0.244 | 0.122 | 0.031 | 0.976 | 3.90 | 0.031 | 3.90 | B |
| 37 | 3,4-dimethoxyphenyl | 0.244 | 0.122 | 0.0152 | 0.488 | 1.95 | 0.061 | 1.95 | B |
| 38 | 3,4-(methylenedioxy)phenyl | 7.81 | 1.95 | 0.244 | 7.81 | 15.6 | 1.95 | 31.3 | B |
| 39 | 3,4,5-trimethoxyphenyl | 0.122 | 0.061 | 0.0152 | 0.976 | 3.90 | 0.122 | 7.81 | B |
| 40 | 4-ethoxyphenyl | 1.95 | 0.488 | 0.122 | 1.95 | 7.81 | 3.90 | 7.81 | B |
| 41 | 3-thienyl | 0.976 | 0.976 | 0.0152 | 0.244 | 0.976 | 0.061 | 1.95 | B |
| 42 | 4-thiazolyl | 0.488 | 0.244 | 0.0038 | 0.244 | 0.976 | 0.122 | 0.976 | B |
| 43 | 2-pyridinyl | 0.976 | 0.488 | <0.0009 | 0.488 | 0.244 | 0.061 | 0.244 | A |
| 44 | 3-pyridinyl | 7.81 | 0.976 | <0.0009 | 0.488 | 0.488 | 0.122 | 7.81 | A |
| 45 | 4-pyridinyl | 0.122 | 0.122 | 0.0038 | 0.244 | 0.488 | 0.122 | 0.488 | A |
| 46 | benzo[b]thien-3-yl | 31.3 | 31.3 | 1.95 | 125 | >250 | 15.6 | >250 | B |
| 47 | 1-naphthalenyl | 3.90 | 0.976 | 0.0019 | 15.6 | 62.5 | 0.976 | 31.3 | A |
| 48 | 2-naphthalenyl | 125 | 125 | 0.244 | 250 | >250 | 7.81 | >250 | A |
| 49 | 2-methyl-1-naphthalenyl | 125 | 125 | 0.122 | >250 | >250 | 15.6 | >250 | B |
| 50 | 2-quinolinyl | 0.976 | 0.488 | 0.0038 | 7.81 | 7.81 | 0.122 | 7.81 | A |
| 51 | 8-quinolinyl | 0.244 | 0.122 | 0.0152 | 0.244 | 1.95 | 0.122 | 7.81 | B |
| 52 | 3,5-dimethyl-4-isoxazolyl | 1.95 | 0.976 | 0.0152 | 0.976 | 1.95 | 0.244 | 3.90 | B |
| 53 | n-hexyl | 31.3 | 15.6 | 0.488 | 31.3 | 62.5 | 3.90 | 250 | B |
| 54 | cyclohexyl | 7.81 | 3.90 | 0.0152 | 1.95 | 7.81 | 0.488 | 3.90 | A |
| 55 | 2-methyl-1-propenyl | 1.95 | 0.976 | 0.0038 | 3.90 | 7.81 | 0.488 | 7.81 | A |
| 56 | 2-phenylethyl | 250 | 250 | 250 | 250 | 250 | 250 | 250 | A |
| 57 | 2-phenylvinyl | 1.95 | 0.976 | 0.122 | 3.90 | 15.6 | 0.488 | 7.81 | B |
| 58 | 3,5-dimethoxyphenyl | 0.488 | 0.244 | 0.061 | 0.976 | 1.95 | 0.122 | 15.6 | B |
| 59 | 2-thienyl | 0.244 | 0.061 | 0.0019 | 0.061 | 0.244 | 0.061 | 0.244 | B |
| 60 | 1-bromo-2-naphthalenyl | 31.3 | 15.6 | 0.488 | >250 | >250 | 15.6 | >250 | B |
| 61 | 4-acetylphenyl | 0.244 | 0.122 | 0.0076 | 0.488 | 0.976 | 0.061 | 1.95 | B |
| 62 | 3-aminophenyl[f] | 0.488 | 0.244 | 0.061 | 0.244 | 0.976 | 0.122 | 1.95 | B |
| 63 | 4-(methylsulfonyl)phenyl | 0.122 | 0.122 | 0.0152 | 0.976 | 0.976 | 0.122 | 7.81 | B |
| 64 | 4-(trifluoromethoxy)phenyl | 0.976 | 0.244 | 0.031 | 3.90 | 62.5 | 0.122 | 62.5 | B |
| 65 | hydrogen[g] | 62.5 | 7.81 | 0.031 | 0.976 | 3.90 | 1.95 | 1.95 | A |
| 66 | 2-methylpropyl[h] | 1.95 | 0.976 | 0.0038 | 0.976 | 3.90 | 0.244 | 3.90 | A |
| 67 | tetrahydro-2-furanyl[i] | 3.90 | 0.976 | 0.0038 | 1.95 | 7.81 | 0.488 | 3.90 | A |
| 68 | 4-carboxyphenyl, sodium salt | 250 | 250 | 62.5 | >250 | >250 | >250 | 250 | B |

[a]Growth medium* A = Seed agar with 5% hemolyzed horse blood. B = Wellcotest Sensitivity Test Agar with 5% hemolyzed horse blood.
[b]This compound is tested as the free diamine.
[c]This compound, prepared in the manner recorded in Example 5, is isolated and tested as the hydrate bearing one-fourth molecule of water per molecule of diamine, m.p. 198-199°.
[d]This compound, prepared in the manner recorded in Example 15, is isolated and tested as the hydrate bearing one-fourth molecule of water per molecule of diamine, m.p. 240°.
[e]This compound, prepared in the manner recorded in Example 18, is isolated and tested as the hydrate bearing one-eighth molecule of water per molecule of diamine, m.p. 246°.
[f]This compound is tested as the dihydrochloride, monohydrate, salt.
[g]This compound is tested as the monoacetate salt.
[h]This compound is tested as the monohydrochloride, hemihydrate salt.
[i]This compound is tested as the monohydrochloride salt bearing one-third molecule of water per molecule of diamine salt.

TABLE V

In vitro Antibacterial Activity of 7-Substituted-7H-Pyrrolo[3,2-f]Quinazoline-1,3-Diamines

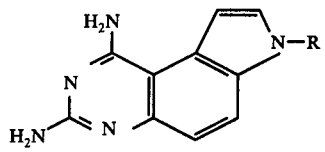

| | | | | | MIC (γ/ml.) | | | | |
|---|---|---|---|---|---|---|---|---|---|
| Compound of Example | R | S. aureus Smith | S. aureus 53-180 | N. catarrhalis 8193 | E. coli 9637 | S. paratyphi 11737 | K. pneumoniae 10031 | P. vulgaris 6896 | Medium[a] |
| 1 | hydrogen[b] | 31.3 | 31.3 | 0.244 | 3.90 | 31.3 | 7.81 | 15.6 | A |
| 69 | 4-cyanophenyl | 0.976 | 0.488 | 0.031 | 0.976 | 31.3 | 0.122 | 125 | B |
| 70 | 2-acetylphenyl | 0.061 | 0.031 | 0.0076 | 0.244 | 0.488 | 0.0152 | 0.976 | B |
| 71 | 4-acetylphenyl | 1.95 | 0.488 | 0.031 | 0.976 | 7.81 | 0.122 | 15.6 | B |
| 72 | 4-propionylphenyl | 31.3 | 7.81 | 0.031 | 15.6 | >250 | 31.3 | >250 | B |
| 73 | 2-cyanophenyl | 0.031 | 0.0152 | 0.0038 | 0.122 | 0.122 | 0.0152 | 0.488 | B |
| 74 | 4-(methylsulfonyl)phenyl | 0.976 | 0.976 | 0.0152 | 0.976 | 7.81 | 0.244 | 15.6 | B |
| 75 | 4-carbethoxyphenyl | 125 | 7.81 | 0.122 | >250 | >250 | 250 | >250 | B |
| 76 | 2-nitrophenyl | 0.244 | 0.244 | 0.031 | 0.976 | 1.95 | 0.244 | 3.90 | B |
| 77 | 4-nitrophenyl | 3.90 | 3.90 | 0.031 | 7.81 | 62.5 | 0.976 | 250 | B |
| 78 | 2,4-dinitrophenyl | 0.0076 | 0.0076 | 0.0019 | 3.90 | >250 | 0.031 | >250 | B |
| 79 | 2-cyano-4-nitrophenyl | 0.488 | 0.488 | 0.244 | 15.6 | >250 | 1.95 | >250 | B |
| 80 | 3-methyl-4-nitrophenyl | 62.5 | 7.81 | 0.0152 | >250 | >250 | 0.976 | >250 | B |
| 81 | 2-thiazolyl | 0.488 | 0.244 | 0.0152 | 0.976 | 1.95 | 0.244 | 3.90 | B |
| 82 | 5-nitro-2-pyridinyl | 0.976 | 3.90 | 0.031 | >250 | >250 | 31.3 | >250 | B |
| 83 | 2-pyridinyl | 0.976 | 0.488 | 0.0076 | 0.488 | 0.976 | 0.244 | 0.976 | B |
| 84 | 2-pyrimidinyl | 15.6 | 3.90 | 0.061 | 7.81 | >250 | 0.976 | >250 | B |
| 85 | 2-pyrazinyl | 3.90 | 1.95 | 0.122 | 0.976 | 3.90 | 0.976 | 3.90 | B |
| 86 | 2-quinolinyl | >250 | >250 | 0.122 | >250 | >250 | >250 | >250 | B |
| 87 | 4-quinolinyl | 0.031 | 0.0152 | 0.031 | 0.488 | 0.976 | 0.031 | 1.95 | B |
| 88 | 4-methyl-2-quinolinyl | 62.5 | 31.3 | 0.061 | 62.5 | >250 | 31.3 | >250 | B |
| 89 | 7-chloro-4-quinolinyl | 0.488 | 0.122 | 0.244 | 15.6 | >250 | 0.488 | 250 | B |
| 90 | 7-trifluoromethyl-4-quinolinyl | 0.122 | 0.031 | 0.031 | 0.244 | 31.3 | 0.244 | 250 | B |
| 91 | 2-methyl-4-quinolinyl | 0.061 | 0.061 | 0.031 | 1.95 | 1.95 | 0.061 | 3.90 | B |
| 92 | 3-methyl-2-quinoxalinyl | 1.95 | 0.488 | 0.122 | 7.81 | >250 | 0.976 | >250 | B |
| 93 | 2-trifluoromethylphenyl | 0.061 | 0.031 | 0.0076 | 0.244 | 0.976 | 0.061 | 1.95 | B |
| 94 | 2-trifluoromethyl-4-nitrophenyl | 0.122 | 0.122 | 0.061 | 31.3 | 62.5 | 0.488 | 125 | B |
| 95 | 2-phenyl-4-quinolinyl | 31.3 | 7.81 | 15.6 | 250 | >250 | 250 | >250 | B |
| 96 | 4-aminophenyl | 0.488 | 0.244 | 0.0152 | 0.244 | 0.488 | 0.031 | 0.976 | B |
| 97 | 2-benzothiazolyl | 250 | 125 | 0.488 | >250 | >250 | 62.5 | >250 | B |

[a]Growth medium: A = Seed agar with 5% hemolyzed horse blood. B = Wellcotest Sensitivity Test Agar with 5% hemolyzed horse blood.
[b]This compound is tested as the hydrochloride salt.

TABLE VI

In vitro Antibacterial Activities of 7,8-Substituted-7H-Pyrrolo[3,2-f]Quinazoline-1,3-Diamines

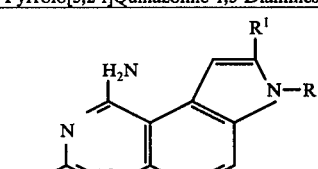

| | | | | | | MIC (γ/ml.) | | | | |
|---|---|---|---|---|---|---|---|---|---|---|
| Compound of Example | R | $R_1$ | S. aureus Smith | S. aureus 53-180 | N. catarrhalis 8193 | E. coli 9637 | S. paratyphi 11737 | K. pneumoniae 10031 | P. vulgaris 6896 | Medium[a] |
| 98 | hydrogen | methyl | 31.3 | 31.3 | 1.95 | 3.90 | 15.6 | 3.90 | 15.6 | B |
| 99 | methyl | methyl | 31.3 | 31.3 | 0.061 | 0.244 | 1.95 | 0.244 | 0.976 | B |
| 100 | benzyl | methyl | 1.95 | 0.976 | 0.122 | 0.488 | 3.90 | 0.244 | 15.6 | B |
| 101 | 3-cyanobenzyl | methyl | 0.122 | 0.061 | 0.0038 | 0.488 | 3.90 | 0.061 | 3.90 | B |
| 102 | 4-cyanobenzyl | methyl | 0.976 | 0.976 | 0.061 | 1.95 | 7.81 | 0.244 | 31.3 | B |
| 103 | 2,5-di- | methyl | 31.3 | 7.81 | 1.95 | 250 | >250 | 15.6 | >250 | B |

TABLE VI-continued

In vitro Antibacterial Activities of 7,8-Substituted-7H-Pyrrolo[3,2-f]Quinazoline-1,3-Diamines

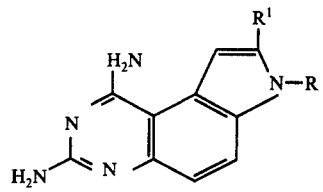

| Compound of Example | R | $R_1$ | S. aureus Smith | S. aureus 53–180 | N. catarrhalis 8193 | E. coli 9637 | S. para-typhi 11737 | K. pneumoniae 10031 | P. vulgaris 6896 | Medium[a] |
|---|---|---|---|---|---|---|---|---|---|---|
| 104 | methyl-benzyl | chloro | 3.90 | 0.976 | 0.061 | 3.90 | 7.81 | 0.244 | 31.3 | B |
| 105 | hydrogen | phenyl | 7.81 | 15.6 | 62.5 | 62.5 | 125 | 31.3 | >250 | B |
| 106 | methyl | phenyl | 62.5 | 125 | 31.3 | >250 | >250 | 3.90 | >250 | B |

[a]Growth medium: B = Wellcotest Sensitivity Agar with 5% hemolyzed horse blood.

TABLE VII

In vitro Antibacterial Activities of 7-Substituted-8,9,10,11-Tetrahydro-7H-Pyrimido[4,5-c]Carbazole-1,3-Diamines

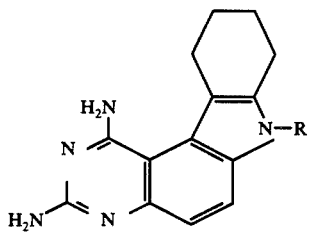

| Compound of Example | R | S. aureus Smith | S. aureus 53–180 | N. catarrhalis 8193 | E. coli 9637 | S. para-typhi 11737 | K. pneumoniae 10031 | P. vulgaris 6896 | Medium[a] |
|---|---|---|---|---|---|---|---|---|---|
| 107 | hydrogen | 62.5 | 125 | 125 | 125 | 125 | 125 | >250 | B |
| 108 | benzyl | >250 | 250 | 0.122 | >250 | >250 | >250 | >250 | B |
| 109 | methyl | 62.5 | 62.5 | 3.90 | >250 | 250 | 62.5 | >250 | B |

[a]Growth Medium: B = Wellcotest Sensitivity Agar with 5% hemolyzed horse blood.

EXAMPLE 111

The ability of compounds of this invention to demonstrate synergistic action against antibacterial infections in mice when administered with sulfomethoxazole is demonstrated in the following test procedure:

The test agents are weighed, suspended in 0.5% aqueous carboxymethyl cellulose, homogenized (glass tissue grinder) and diluted according to the design of the experiment. Mice (male, 18±1 g., CD-1 strain) are preweighed, pooled, infected at random intraperitoneally with a 0.5 ml. standardized suspension ($LD_{95} \pm 5\%$) of the bacterial organism in 5% gastric mucin and treated at random with single doses of the test agents either at the time of infection or six hours after infecting. The treated groups consist of ten mice per dosage level. Deaths are recorded daily for 14 days and the $PD_{50}$ (mice are treated at time of infection) and $CD_{50}$ (mice are treated six hours after infecting) values are calculated by the method of Reed and Muench [Amer. J. Hyg., 27, 493 (1938)].

TABLE VIII

In vivo Antibacterial Synergism Data (Mouse) for 7,8-Substituted -7H-Pyrrolo[3,2-f]Quinazoline-1,3-Diamines

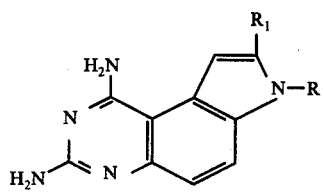

$PD_{50}{}^a$ or $CD_{50}{}^b$ Values, mg. per kg., p.o.

| Compound of Example | R | $R_1$ | Organism | Hours[c] | Cpd. | SM[d] | SM/Cpd. |
|---|---|---|---|---|---|---|---|
| 2 | benzyl[e] | H | Proteus mirabilis 190 | 0 | 22.5 | 8.2 | 1.56/7.78 |

TABLE VIII-continued
In vivo Antibacterial Synergism Data (Mouse) for 7,8-Substituted -7H-Pyrrolo[3,2-f]Quinazoline-1,3-Diamines

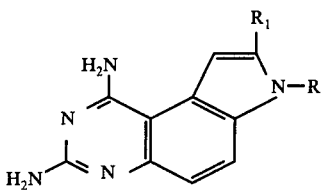

PD$_{50}$$^a$ or CD$_{50}$$^b$ Values, mg. per kg., p.o.

| Compound of Example | R | R$_1$ | Organism | Hours$^c$ | Cpd. | SM$^d$ | SM/Cpd. |
|---|---|---|---|---|---|---|---|
| 5 | 4-fluoro-benzyl | H | Proteus mirabilis 190 | 0 | 9.8 | 7.4 | 1.56/1.56 |
| 16 | 4-cyano-benzyl$^f$ | H | Proteus mirabilis 3 | 0 | 22.7 | 9.9 | 6.25/2.11<br>3.13/2.28<br>1.56/6.56<br>0.78/7.11 |
| 16 | 4-cyano-benzyl$^f$ | H | Proteus vulgaris 347 | 0 | >200 | 43.2 | 6.25/6.25<br>3.13/9.67<br>1.56/>12.5<br>0.78/>12.5 |
| 16 | 4-cyano-benzyl$^f$ | H | Proteus vulgaris 347 | 6 | >400 | 60 | 25/5.07<br>12.5/4.66<br>6.25/8.83<br>3.11/7.28 |
| 16 | 4-cyano-benzyl$^f$ | H | Escherichia coli W-102 | 0 | >800 | 95 | 25.0/15.9<br>12.5/15.6<br>6.25/53.1<br>3.13/67.8 |
| 16 | 4-cyano-benzyl$^f$ | H | Escherichia coli W-102 | 6 | >400 | 356<br>50/37 | 100/37<br>25/89<br>12.5/50 |
| 16 | 4-cyano-benzyl$^f$ | H | Proteus mirabilis 190 | 0 | 18.6 | 7.61 | 3.11/2.44<br>1.56/3.39<br>0.78/8.78<br>0.39/>12.50 |
| 16 | 4-cyano-benzyl$^f$ | H | Proteus mirabilis 190 | 6 | 159 | 14 | 3.11/2.33<br>1.56/4.0<br>0.78/>6.25<br>0.39/>6.25 |
| 100 | benzyl | Me | Proteus mirabilis 190 | 0 | 36.6 | 5.1 | 1.56/3.11 |
| 15 | 3-cyano-benzyl$^g$ | H | Proteus mirabilis 190 | 0 | 8.8 | 7.6 | 1.56/2.67 |
| 69 | 4-cyano-phenyl$^h$ | H | Proteus mirabilis 190 | 0 | >400 | 6.25 | 3.11/2.55<br>1.56/9.39<br>0.78/>12.5<br>0.39/>12.5 |
| 81 | 2-thiazolyl$^h$ | H | Proteus mirabilis 190 | 0 | 22.3 | 12.5 | 3.11/6.25<br>1.56/>12.5 |

$^a$This value is the dose required to protect half of the mice from death when the mice are treated immediately after infecting.
$^b$This value is the dose required to protect half of the mice from death when the mice are treated 6 hours after infecting.
$^c$This value is the number of hours elapsing between infecting and dosing of the mice.
$^d$SM=sulfomethoxazole
$^e$This compound is tested as the free diamine.
$^f$This compound, prepared in the manner recorded in Example 16, is isolated and tested as the hydrate bearing one-fifth molecule of water per molecule of diamine, m.p. 247-253° (softens 150°).
$^g$This compound, prepared in the manner recorded in Example 15, is isolated and tested as the hydrate bearing one-fourth molecule of water per molecule of diamine, m.p. 240°.
$^h$In this experiment, groups of five mice are used at each dose level.

EXAMPLE 112

The antimalarial effects of the compounds of Formula I are demonstrated, and elicited by means of the test procedure described below:

Utilizing young ICR/HA Swiss mice and a standard inoculum of Plasmodium berghei KBG 173, it is possible to produce a uniform disease fatal to 100% of untreated animals within 6 to 8 days with a mean survival time of 6.2 days. Test animals weigh from 18 to 22 grams but weight variations in any given experimental or control group are confined to 2-3 grams. All animals in any given test are approximately of the same age. Animals on test are housed in metal-topped plastic cages, given a standard laboratory diet and water ad libitum.

Test animals receive an intraperitoneal injection of 0.5 ml. of 1:100 dilution of heparinized heart's blood with a minimum of 90% parasitized cells (4 × 10$^7$ cells), drawn from donor mice infected one week earlier with Plasmodium berghei. The donor strain is maintained by weekly passages in separate groups of mice inoculated with a 0.5 ml. of 1:500 dilution of heparinized heart's blood.

Test compounds are administered after dissolution or suspension in peanut oil. A single dose is given subcutaneously 72 hours after the mice are infected with Plasmodium berghei. At this time a 10-15 percent parasitemia has developed; the disease is well established but has not produced sufficient debility to alter the response of the host to toxic effects of the drug on test. Since treatment is withheld for three days to permit the infection to become well established and death occurs in untreated controls within 6-8 days, it is felt that this system presents a candidate compound with the maximum challenge. In order to check factors such as changes in the infectivity of Plasmodium berghei or in the susceptibility of the host or to detect technical errors, a group of infected animals treated with pyrimethamine at dose levels producing definite increases in survival time is included in a positive control in every experiment.

In each experiment test compounds are administered in graded dosages. With highly active compounds, increases in dose levels are usually followed by increases in the survival time of the treated mice. However, if an active drug is toxic for the host, its toxicity may become a limiting factor; continued increases in dose levels also increase the toxic effects and may result in the diminution of survival times. Deaths prior to the sixth day, when untreated controls begin to die, are regarded as nonparasitic and become the basis for toxicity evaluations. Treated animals are kept under observation for 60 days. Survivors at the end of this period of time are considered as cured. In calculating mean survival time, toxic deaths and 60-day survivors are not included.

Compounds are considered active which produce a cure in at least one test animal or which produce significant increases in mean survival times of the treated animals as compared with the mean survival times of untreated controls, provided that no drug related deaths (toxicity) are noted at the active dose.

The results of antimalarial testing of compounds of this invention are set forth in Tables IX, X, and XI.

TABLE IX

Activity of 7-(Substituted)Methyl-7H-Pyrrolo[3,2-f]Quinazoline-1,3-Diamines Against Plasmodium berghei KGB 173 Malaria in Mice (All Doses are mg. per kg., s.c. administration)

| Compound of Example | R | Highest Non-Lethal Dose[a] | Lowest Dose Curing All Mice | Min. Curing Dose (Cure/Treat) | ΔMST[b] | Dose |
|---|---|---|---|---|---|---|
| 2 | phenyl[c] | 160 | 80 | 20 (2/5)[d] | 10.9 | 20[d] |
| 3 | 2-fluorophenyl | 80 | 80 | 10 (3/5) | 9.8 | 5 |
| 4 | 3-fluorophenyl | 40 | 40 | 10 (1/5) | 8.3 | 10 |
| 5 | 4-fluorophenyl[e] | 80 | 20 | 5 (2/5) | 7.1 | 2.5 |
| 6 | 2-chlorophenyl | 160 | 20 | 20 (5/5) | 8.3 | 5 |
| 7 | 3-chlorophenyl | 160 | 10 | 2.5 (2/5) | 7.7 | 1.25 |
| 8 | 4-chlorophenyl | 40 | 20 | 10 (2/5) | 8.1 | 5 |
| 10 | 3,4-dichlorophenyl | 40 | 10 | 2.5 (2/5) | 10.2 | 2.5 |
| 12 | 3-trifluoromethylphenyl | — | — | 5 (1/5) | 7.5 | 2.5 |
| 14 | 2-cyanophenyl | 160 | 40 | 10 (1/5) | 8.9 | 10 |
| 15 | 3-cyanophenyl[f] | 40 | 10 | 1.25 (2/5) | 9.6 | 1.25 |
| 16 | 4-cyanophenyl[g] | — | — | 5 (1/5) | 8.4 | 10 |
| 18 | 3-nitrophenyl[h] | 40 | 10 | 2.5 (3/5) | 7.4 | 2.5 |
| 19 | 2-methylphenyl | — | — | 40 (3/5) | 8.4 | 40 |
| 20 | 3-methylphenyl | 320 | 20 | 5 (4/5) | 6.9 | 5 |
| 21 | 4-methylphenyl | 160 | 20 | 10 (2/5) | 7.5 | 5 |
| 23 | 2,5-dimethylphenyl | 640[i] | 40 | 10 (3/5) | 7.9 | 5 |
| 27 | 2,4,6-trimethylphenyl | 80 | 40 | 5 (3/5) | 7.3 | 2.5 |
| 29 | 4-isopropylphenyl | 20 | 20 | 10 (1/5) | 10.2 | 10 |
| 32 | 2-methoxyphenyl | 160 | 40 | 10 (3/5) | 10.5 | 10 |
| 34 | 4-methoxyphenyl | 160 | 20 | 5 (2/5) | 11.2 | 5 |
| 37 | 3,4-dimethoxyphenyl | 80 | 20 | 10 (1/5) | 6.9 | 2.5 |
| 39 | 3,4,5-trimethoxyphenyl | 160 | 160 | 40 (2/5) | 7.1 | 20 |
| 43 | 2-pyridinyl | 80 | 80 | 20 (2/5) | 11.6 | 20 |
| 44 | 3-pyridinyl | 160 | 160 | 80 (3/5) | 8.3 | 40 |
| 45 | 4-pyridinyl | — | — | 80 (3/5) | 9.7 | 40 |
| 47 | 1-naphthalenyl | 80 | 20 | 5 (2/5) | 9.2 | 5 |
| 48 | 2-naphthalenyl | 1160 | 40 | 20 (4/5) | 7.3 | 5 |
| 49 | 2-methyl-1-naphthalenyl | 80 | 20 | 20 (5/5)[d] | — | — |
| 50 | 2-quinolinyl | 160 | 5 | 1.25 (2/5) | 6.9 | 1.25 |
| 51 | 8-quinolinyl | 40 | 20 | 5 (1/5) | 6.4 | 5 |
| 53 | n-hexyl | 640[i] | 640 | 320 (2/5) | 9.5 | 160 |
| 54 | cyclohexyl | — | — | — — | 8.5 | 40 |
| 55 | 2-methyl-1-propenyl | — | — | 640 (3/5) | 9.3 | 320 |
| 56 | 2-phenylethyl | 640[i] | 320 | 160 (3/5) | 10.7 | 80 |
| 61 | 4-acetylphenyl | 40 | 20 | 2.5 (4/5) | 12.0 | 5 |
| 63 | 4-(methylsulfonyl)phenyl | — | — | 10 (1/5) | 6.5 | 5 |
| 66 | 2-methylpropyl[j] | — | — | — — | 8.1 | 320 |
| 9 | 2,6-dichlorophenyl | 160[k] | 40[k] | 5[k] (1/5) | — | — |
| 11 | 2-trifluoromethylphenyl | 40 | 10 | 1.25 (1/5) | 7.3 | 0.63 |
| 25 | 3,4-dimethylphenyl | 80[k] | 10[k] | 5[k] (2/5) | 6.5[k] | 2.5[k] |
| 31 | 4-(methylthio)phenyl | 40[k] | 20[k] | 2.5[k] (4/5) | 6.2[k] | 1.25[k] |
| 33 | 3-methoxyphenyl | 40 | 40 | 10 (1/5) | 7.6 | 5 |
| 38 | 3,4-(methylenedioxy)phenyl | — | — | 10 (2/5) | 12.2 | 2.5 |
| 41 | 3-thienyl | 320[k] | 160[k] | 20[k] (3/5) | — | — |

TABLE IX-continued

Activity of 7-(Substituted)Methyl-7H-Pyrrolo[3,2-f]Quinazoline-1,3-Diamines Against *Plasmodium berghei* KGB 173 Malaria in Mice (All Doses are mg. per kg., s.c. administration)

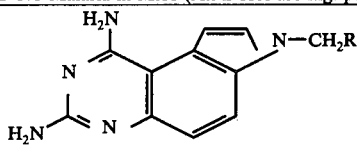

| Compound of Example | R | Highest Non-Lethal Dose[a] | Lowest Dose Curing All Mice | Min. Curing Dose (Cure/Treat) | ΔMST[b] | Dose |
|---|---|---|---|---|---|---|
| 62 | 3-aminophenyl | 80 | 20 | 5 (3/5) | 7.8 | 1.25 |
| 64 | 4-trifluoromethoxyphenyl | 10 | 10 | 2.5 (2/5) | 9.6 | 1.25 |
| 17 | 4-carbethoxyphenyl | 80 | 20 | 10 (1/5) | 6.0 | 2.5 |
| 22 | 2,4-dimethylphenyl | 80[k] | 5[k] | 5[k] (5/5) | 7.6[k] | 2.5[k] |

[a]This is the highest dose with no deaths for any reason.
[b]This abbreviation indicates the increase in mean survival time of treated animals as compared to untreated controls at the dose indicated in the adjacent column.
[c]This compound is tested as the monoacetate salt described in Example 2.
[d]This is the lowest dose tested.
[e]See Table IV, footnote c.
[f]See Table IV, footnote d.
[g]See Table VIII, footnote f.
[h]See Table IV, footnote e.
[i]This is the highest dose tested.
[j]See Table IV, footnote h.
[k]Mice alive on day 14 considered as "cured", no 60-day data available.

TABLE X

Activity of 7,8-Substituted-7H-Pyrrolo[3,2-f]Quinazoline-1,3-Diamines Against *Plasmodium berghei* KBG 173 Malaria in Mice (All Doses Are mg. per kg., s.c. Administration)

| Compound of Example | R | R₁ | Highest Non-Lethal Dose[a] | Lowest Dose Curing All Mice | Min. Curing Dose (Cure/Treat) | ΔMST[b] | Dose |
|---|---|---|---|---|---|---|---|
| 98 | hydrogen | methyl | — | — | 160 (3/5) | 13.9 | 160 |
| 103 | 2,5-dimethylbenzyl | methyl | 80[c] | 5[c] | 1.25[c] (1/5) | 6.8[c] | 1.25[c] |

[a]This is the highest dose with no deaths for any rason.
[b]This abbreviation indicates the increase in mean survival time of treated animals as compared to untreated controls at the dose indicated in the adjacent column.
[c]Mice alive on day 14 considered as "cured", no 60-day data available.

TABLE XI

Activity of 7-Substituted-7H-Pyrrolo[3,2-f]Quinazoline-1,3-Diamines *Plasmodium berghei* KBG 173 Malaria in Mice (All Doses Are in mg. per kg. s.c. Administration)

| Compound of Example | R | Highest Non-Lethal Dose[a] | Lowest Dose Curing All Mice | Min. curing Dose (Cure/Treat) | ΔMST[b] | Dose |
|---|---|---|---|---|---|---|
| 69 | 4-cyanophenyl | 20 | 20 | 5 (3/5) | 11 | 2.5 |
| 70 | 2-acetylphenyl | — | — | 40 (1/5) | 9.2 | 40 |
| 71 | 4-acetylphenyl | — | — | 40 (1/5) | 8.8 | 20 |
| 76 | 2-nitrophenyl | — | — | 40 (4/5) | — | — |
| 77 | 4-nitrophenyl | 640 | 640 | 160 (5/5) | 28.3 | 40 |
| 80 | 3-methyl-4-nitro | 640 | 640 | 640 (5/5) | 13.9 | 160 |
| 81 | 2-thiazolyl | — | — | 640 (4/5) | 8.3 | 160 |
| 82 | 5-nitro-2-pyridinyl | — | — | 160[c] (1/5) | — | — |

[a]This is the highest dose with no deaths for any reason.
[b]This abbreviation indicates the increase in mean survival time of treated animals as compared to untreated controls at the dose indicated in the adjacent column.
[c]Mice alive on day 14 considered as "cured", no 60-day data available.

EXAMPLE 113

Single doses of 7-(phenylmethyl)-7H-pyrrolo[3,2-f]-quinazoline-1,3-diamine (active moiety) were intraperitoneally administered in 0.5% carboxymethylcellulose at a constant dose volume of 10 ml./kg., to groups of 10 mice/dose level. (Charles River COBS CD Strain Albino mice, male, weight 21.0–25.29.) Daily observations were made on all mice for the duration of experiment (14 days). The resulting $LD_{50}$ was 54.5 mg./kg. (95% confidence limits of 48.6–93.4) all deaths occurred 4–5 days post-drug-administration.

The compound produced decreased spontaneous motor activity, bradypnea, ptosis, and stretching with indrawn sides in all mice within 1 hour after i.p. injection. In addition, rough coats and decreased fecal elimination were observed on day 2 post-drug-administration. These effects lasted up to 6 days in the low dose animals and 14 days in those animals having received the highest dose. All mice alive on day 14 were sacrificed and necropsied. Macroscopically, the tissues appeared normal.

What is claimed is:

1. A compound of the general formula:

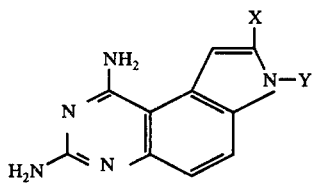

or a non-toxic acid addition salt thereof, wherein:
(a) X is hydrogen and Y is —$CH_2R$ or —$R^1$ wherein:

R is hydrogen; methyl; ethyl; n-propyl; i-propyl; n-butyl; i-butyl; n-pentyl; n-hexyl; 2-methyl-1-propenyl; cyclobutyl; cyclopentyl; cyclohexyl; 2-phenylethyl; 2-phenylvinyl; phenyl; phenyl monosubstituted in the 2-, 3-, or 4-position by chlorine, bromine, iodine, fluorine, trifluoromethyl, methyl, ethyl, n-propyl, i-propyl, n-butyl, i-butyl, t-butyl, methoxy, ethoxy, n-propoxy, trifluoromethoxy, cyano, methylsulfonyl, acetyl, propionyl, methylthio, ethylthio, carbethoxy, carboxyl, sodium carboxy, or potassium carboxy; phenyl monosubstituted in the 3-position by amino or nitro; phenyl disubstituted in the 2,3-, 2,4-, 2,5-, 2,6-, 3,4-, or 3,5-positions by methyl, ethyl, n-propyl, methoxy, ethoxy, n-propoxy, chlorine, bromine, iodine, or fluorine; phenyl trisubstituted in the 2,4,6- or 3,4,5-positions by methyl, ethyl, methoxy, or ethoxy; 2,3,5,6-tetramethylphenyl; 3,4-(methylene dioxy)-phenyl; 1-naphthalenyl; 2-naphthalenyl; 2-methyl-1-naphthalenyl; 1-bromo-2-naphthalenyl; 2-pyridinyl; 3-pyridinyl; 4-pyridinyl; 2-quinolinyl; 8-quinolinyl; 2-thienyl; 3-thienyl; 4-thiazolyl; 3,5-dimethyl-4-isoxazolyl; tetrahydro-2-furanyl; or benzo[b]thien-3-yl; and $R^1$ is hydrogen; phenyl monosubstituted in the 2- or 4-position by amino, nitro, cyano, acetyl, propionyl, methylsulfonyl, trifluoromethyl, or carbethoxy; 2,4-dinitrophenyl; 2,4-diaminophenyl; 2-cyano-4-nitrophenyl; 2-cyano-4-aminophenyl; 3-methyl-4-nitrophenyl; 3-methyl-4-aminophenyl; 2-trifluoromethyl-4-nitrophenyl; 2-trifluoromethyl-4-aminophenyl; 2-thiazolyl; 2-pyridinyl; 5-nitro-2-pyridinyl; 2-pyrimidinyl; 2-pyrazinyl; 2-quinolinyl; 4-quinolinyl; 4-methyl-2-quinolinyl; 7-chloro-4-quinolinyl; 7-trifluoromethyl-4-quinolinyl; 2-methyl-4-quinolinyl; 3-methyl-2-quinoxalinyl; 2-phenyl-4-quinolinyl; or 2-benzothiazolyl; and (b) X is methyl, phenyl, or chlorine; and Y is hydrogen, methyl, benzyl, 3-cyanobenzyl, 4-cyanobenzyl, or 2,5-dimethylbenzyl; provided that when X is phenyl, Y may only be hydrogen or methyl, and when X is chlorine, Y may only be benzyl.

2. A compound as defined in claim 1 wherein
X is hydrogen;
Y is —$CH_2$—R; and
R is hydrogen; methyl; ethyl; n-propyl; i-propyl; n-butyl; i-butyl; n-pentyl; n-hexyl; 2-methyl-1-propenyl; cyclobutyl; cyclopentyl; cyclohexyl; 2-phenylethyl; 2-phenylvinyl; phenyl; phenyl monosubstituted in the 2-, 3-, or 4-position by chlorine, bromine, iodine, fluorine, trifluoromethyl, methyl, ethyl, n-propyl, i-propyl, n-butyl, i-butyl, t-butyl, methoxy, ethoxy, n-propoxy, trifluoromethoxy, cyano, methylsulfonyl, acetyl, propionyl, methylthio, ethylthio, carbethoxy, carboxyl, sodium carboxy, or potassium carboxy; phenyl monosubstituted in the 3-position by amino or nitro; phenyl disubstituted in the 2,3-, 2,4-, 2,5-, 2,6-, 3,4-, or 3,5-positions by methyl, ethyl, n-propyl, methoxy, ethoxy, n-propoxy, chlorine, bromine, iodine, or fluorine; phenyl trisubstituted in the 2,4,6- or 3,4,5-positions by methyl, ethyl, methoxy, or ethoxy; 2,3,5,6-tetramethylphenyl; 3,4-(methylene dioxy)-phenyl; 1-naphthalenyl; 2-naphthalenyl; 2-methyl-1-naphthalenyl; 1-bromo-2-naphthalenyl; 2-pyridinyl; 3-pyridinyl; 4-pyridinyl; 2-quinolinyl; 8-quinolinyl; 2-thienyl; 3-thienyl; 4-thiazolyl; 3,5-dimethyl-4-isoxazolyl; tetrahydro-2-furanyl; or benzo[b]thien-3-yl.

3. The compound as defined in claim 2 wherein R is phenyl.

4. The compound as defined in claim 2 wherein R is 2-fluorophenyl.

5. The compound as defined in claim 2 wherein R is 3-fluorophenyl.

6. The compound as defined in claim 2 wherein R is 4-fluorophenyl.

7. The compound as defined in claim 2 wherein R is 2-chlorophenyl.

8. The compound as defined in claim 2 wherein R is 3-chlorophenyl.

9. The compound as defined in claim 2 wherein R is 4-chlorophenyl.

10. The compound as defined in claim 2 wherein R is 2,6-dichlorophenyl.

11. The compound as defined in claim 2 wherein R is 3,4-dichlorophenyl.

12. The compound as defined in claim 2 wherein R is 2-trifluoromethylphenyl.

13. The compound as defined in claim 2 wherein R is 3-trifluoromethylphenyl.

14. The compound as defined in claim 2 wherein R is 4-trifluoromethylphenyl.

15. The compound as defined in claim 2 wherein R is 2-cyanophenyl.

16. The compound as defined in claim 2 wherein R is 3-cyanophenyl.

17. The compound as defined in claim 2 wherein R is 4-cyanophenyl.

18. The compound as defined in claim 2 wherein R is 4-carbethoxyphenyl.

19. The compound as defined in claim 2 wherein R is 3-nitrophenyl.

20. The compound as defined in claim 2 wherein R is 2-methylphenyl.

21. The compound as defined in claim 2 wherein R is 3-methylphenyl.

22. The compound as defined in claim 2 wherein R is 4-methylphenyl.

23. The compound as defined in claim 2 wherein R is 2,4-dimethylphenyl.

24. The compound as defined in claim 2 wherein R is 2,5-dimethylphenyl.

25. The compound as defined in claim 2 wherein R is 2,6-dimethylphenyl.

26. The compound as defined in claim 2 wherein R is 3,4-dimethylphenyl.

27. The compound as defined in claim 2 wherein R is 2,4,6-trimethylphenyl.

28. The compound as defined in claim 2 wherein R is 2,3,5,6-tetramethylphenyl.

29. The compound as defined in claim 2 wherein R is 4-isopropylphenyl.

30. The compound as defined in claim 2 wherein R is 4-t-butylphenyl.

31. The compound as defined in claim 2 wherein R is 4-(methylthio)phenyl.

32. The compound as defined in claim 2 wherein R is 2-methoxyphenyl.

33. The compound as defined in claim 2 wherein R is 3-methoxyphenyl.

34. The compound as defined in claim 2 wherein R is 4-methoxyphenyl.

35. The compound as defined in claim 2 wherein R is 2,3-dimethoxyphenyl.

36. The compound as defined in claim 2 wherein R is 2,5-dimethoxyphenyl.

37. The compound as defined in claim 2 wherein R is 3,4-dimethoxyphenyl.

38. The compound as defined in claim 2 wherein R is 3,4-(methylenedioxy)-phenyl.

39. The compound as defined in claim 2 wherein R is 3,4,5-trimethoxyphenyl.

40. The compound as defined in claim 2 wherein R is 4-ethoxyphenyl.

41. The compound as defined in claim 2 wherein R is 3-thienyl.

42. The compound as defined in claim 2 wherein R is 4-thiazolyl.

43. The compound as defined in claim 2 wherein R is 2-pyridinyl.

44. The compound as defined in claim 2 wherein R is 3-pyridinyl.

45. The compound as defined in claim 2 wherein R is 4-pyridinyl.

46. The compound as defined in claim 2 wherein R is benzo[b]thien-3-yl.

47. The compound as defined in claim 2 wherein R is 1-naphthalenyl.

48. The compound as defined in claim 2 wherein R is 2-naphthalenyl.

49. The compound as defined in claim 2 wherein R is 2-methyl-1-naphthalenyl.

50. The compound as defined in claim 2 wherein R is 2-quinolinyl.

51. The compound as defined in claim 2 wherein R is 8-quinolinyl.

52. The compound as defined in claim 2 wherein R is 3,5-dimethyl-4-isoxazolyl.

53. The compound as defined in claim 2 wherein R is n-hexyl.

54. The compound as defined in claim 2 wherein R is cyclohexyl.

55. The compound as defined in claim 2 wherein R is 2-methyl-1-propenyl.

56. The compound as defined in claim 2 wherein R is 2-phenylethyl.

57. The compound as defined in claim 2 wherein R is 2-phenylvinyl.

58. The compound as defined in claim 2 wherein R is 3,5-dimethoxyphenyl.

59. The compound as defined in claim 2 wherein R is 2-thienyl.

60. The compound as defined in claim 2 wherein R is 1-bromo-2-naphthalenyl.

61. The compound as defined in claim 2 wherein R is 4-acetylphenyl.

62. The compound as defined in claim 2 wherein R is 3-aminophenyl.

63. The compound as defined in claim 2 wherein R is 4-methylsulfonylphenyl.

64. The compound as defined in claim 2 wherein R is 4-trifluoromethoxyphenyl.

65. The compound as defined in claim 2 wherein R is hydrogen.

66. The compound as defined in claim 2 wherein R is isobutyl.

67. The compound as defined in claim 2 wherein R is tetrahydro-2-furanyl.

68. The compound as defined in claim 2 wherein R is 4-(sodium carboxy)phenyl.

69. A compound as defined in claim 1 wherein
X is hydrogen,
Y is $R^1$, and
$R^1$ is hydrogen; phenyl monosubstituted in the 2- or 4-position by amino, nitro, cyano, acetyl, propionyl, methylsulfonyl, trifluoromethyl, or carbethoxy; 2,4-dinitrophenyl; 2,4-diaminophenyl; 2-cyano-4-nitrophenyl; 2-cyano-4-aminophenyl; 3-methyl-4-nitrophenyl; 3-methyl-4-aminophenyl; 2-trifluoromethyl-4-nitrophenyl; 2-trifluoromethyl-4-aminophenyl; 2-thiazolyl; 2-pyridinyl; 5-nitro-2-pyridinyl; 2-pyrimidinyl; 2-pyrazinyl; 2-quinolinyl; 4-quinolinyl; 4-methyl-2-quinolinyl; 7-chloro-4-quinolinyl; 7-trifluoromethyl-4-quinolinyl; 2-methyl-4-quinolinyl; 3-methyl-2-quinoxalinyl; 2-phenyl-4-quinolinyl; or 2-benzothiazolyl.

70. The compound as defined in claim 69 wherein $R^1$ is 4-cyanophenyl.

71. The compound as defined in claim 69 wherein $R^1$ is 2-acetylphenyl.

72. The compound as defined in claim 69 wherein $R^1$ is 4-acetylphenyl.

73. The compound as defined in claim 69 wherein $R^1$ is 4-propionylphenyl.

74. The compound as defined in claim 69 wherein $R^1$ is 2-cyanophenyl.

75. The compound as defined in claim 69 wherein $R^1$ is 4-(methylsulfonyl)phenyl.

76. The compound as defined in claim 69 wherein $R^1$ is 4-carbethoxyphenyl.

77. The compound as defined in claim 69 wherein $R^1$ is 2-nitrophenyl.

78. The compound as defined in claim 69 wherein $R^1$ is 4-nitrophenyl.

79. The compound as defined in claim 69 wherein $R^1$ is 2,4-dinitrophenyl.

80. The compound as defined in claim 69 wherein $R^1$ is 2-cyano-4-nitrophenyl.

81. The compound as defined in claim 69 wherein $R^1$ is 3-methyl-4-nitrophenyl.

82. The compound as defined in claim 69 wherein $R^1$ is 2-thiazolyl.

83. The compound as defined in claim 69 wherein $R^1$ is 5-nitro-2-pyridinyl.

84. The compound as defined in claim 69 wherein $R^1$ is 2-pyridinyl.

85. The compound as defined in claim 69 wherein $R^1$ is 2-pyrimidinyl.

86. The compound as defined in claim 69 wherein $R^1$ is 2-pyrazinyl.

87. The compound as defined in claim 69 wherein $R^1$ is 2-quinolinyl.

88. The compound as defined in claim 69 wherein $R^1$ is 4-quinolinyl.

89. The compound as defined in claim 69 wherein $R^1$ is 4-methyl-2-quinolinyl.

90. The compound as defined in claim 69 wherein $R^1$ is 7-chloro-4-quinolinyl.

91. The compound as defined in claim 69 wherein $R^1$ is 7-trifluoromethyl-4-quinolinyl.

92. The compound as defined in claim 69 wherein $R^1$ is 2-methyl-4-quinolinyl.

93. The compound as defined in claim 69 wherein $R^1$ is 3-methyl-2-quinoxalinyl.

94. The compound as defined in claim 69 wherein $R^1$ is 2-trifluoromethylphenyl.

95. The compound as defined in claim 69 wherein $R^1$ is 2-trifluoromethyl-4-nitrophenyl.

96. The compound as defined in claim 69 wherein $R^1$ is 2-phenyl-4-quinolinyl.

97. The compound as defined in claim 69 wherein $R^1$ is 4-aminophenyl.

98. The compound as defined in claim 69 wherein $R^1$ is 2-benzothiazolyl.

99. The compound as defined in claim 69 wherein $R^1$ is hydrogen.

100. A compound as defined in claim 1 wherein
X is methyl, phenyl, or chlorine; and
Y is hydrogen, methyl, benzyl, 3-cyanobenzyl, 4-cyanobenzyl, or 2,5-dimethylbenzyl; provided that when X is phenyl, Y may only be hydrogen or methyl, and when X is chlorine, Y may only be benzyl.

101. The compound as defined in claim 100 wherein Y is methyl and X is methyl.

102. The compound as defined in claim 100 wherein Y is hydrogen and X is methyl.

103. The compound as defined in claim 100 wherein Y is benzyl and X is methyl.

104. The compound as defined in claim 100 wherein Y is 3-cyanobenzyl and X is methyl.

105. The compound as defined in claim 100 wherein Y is 4-cyanobenzyl and X is methyl.

106. The compound as defined in claim 100 wherein Y is 2,5-dimethylbenzyl and X is methyl.

107. The compound as defined in claim 100 wherein X is chlorine and Y is benzyl.

108. The compound as defined in claim 100 wherein X is phenyl and Y is hydrogen.

109. The compound as defined in claim 100 wherein X is phenyl and Y is methyl.

110. The compound as defined in claim 2 wherein R is 3,5-dimethylphenyl.

* * * * *